(12) United States Patent
Kovarik et al.

(10) Patent No.: US 10,806,408 B2
(45) Date of Patent: *Oct. 20, 2020

(54) METHOD FOR PREVENTING AN INFECTION BY A VIRUS

(71) Applicant: NoHands, LLC, Englewood, CO (US)

(72) Inventors: Katherine Rose Kovarik, Englewood, CO (US); Joseph E. Kovarik, Englewood, CO (US); Mourad Zarouri, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/100,492

(22) Filed: Aug. 10, 2018

(65) Prior Publication Data

US 2018/0360394 A1 Dec. 20, 2018

Related U.S. Application Data

(63) Continuation of application No. 15/195,314, filed on Jun. 28, 2016, now Pat. No. 10,045,742, which is a
(Continued)

(51) Int. Cl.
*A61B 5/00* (2006.01)
*G01N 33/569* (2006.01)
(Continued)

(52) U.S. Cl.
CPC .......... *A61B 5/746* (2013.01); *A61B 5/0026* (2013.01); *A61B 5/1114* (2013.01); *A61B 5/15* (2013.01); *A61B 5/411* (2013.01); *A61B 5/6803* (2013.01); *A61B 5/6804* (2013.01); *A61B 5/6822* (2013.01); *A61B 5/6887* (2013.01); *A61B 5/6891* (2013.01); *A61B 5/6893* (2013.01);
(Continued)

(58) Field of Classification Search
CPC combination set(s) only.
See application file for complete search history.

(56) References Cited

U.S. PATENT DOCUMENTS 4,301,808 A * 11/1981 Taus ................. A61B 5/024
600/500
4,965,553 A * 10/1990 DelBiondo, II ... G08B 21/0453
340/573.1
(Continued)

*Primary Examiner* — Michael W Kahelin
*Assistant Examiner* — Shirley X Jian
(74) *Attorney, Agent, or Firm* — Sheridan Ross P.C.

(57) ABSTRACT

A method for preventing obesity related to infection by an adipogenic adenovirus includes obtaining a sample from a person, assaying the sample to determine whether the person has been previously infected with an adipogenic adenovirus, and if the person has not been previously infected, providing the person with at least one sensor positioned to detect when a person's hand approaches a predetermined distance from the person's face. By warning the person of undesired hand-to-face contacts, the person is able to reduce the incidence of obesity related infections. Other embodiments are directed to a kit for preventing obesity caused by infection with an adipogenic adenovirus, such kit including a container for assaying an agent indicating the presence of antibodies to Ad-36, and a sensor positioned on an item selected from the group consisting of one of a hat, a writing instrument, eye glasses, a belt, sunglasses, a bra, a shirt, and a tie.

9 Claims, 13 Drawing Sheets

Related U.S. Application Data continuation of application No. 14/078,718, filed on Nov. 13, 2013, now Pat. No. 9,408,559, which is a continuation of application No. 12/949,458, filed on Nov. 18, 2010, now Pat. No. 8,591,412, which is a continuation of application No. 13/510,635, filed as application No. PCT/US2010/057248 on Nov. 18, 2010, now Pat. No. 8,585,588.

(60) Provisional application No. 61/262,337, filed on Nov. 18, 2009.

(51) Int. Cl.
*A61B 5/11* (2006.01)
*A61B 5/15* (2006.01)
*A61B 10/00* (2006.01)
*A61F 5/00* (2006.01)

(52) U.S. Cl.
CPC .......... *A61B 5/6897* (2013.01); *A61B 5/6898* (2013.01); *A61B 5/7282* (2013.01); *A61B 5/742* (2013.01); *A61B 5/7405* (2013.01); *A61B 5/7455* (2013.01); *A61B 10/0038* (2013.01); *A61B 10/0051* (2013.01); *A61F 5/0003* (2013.01); *G01N 33/56983* (2013.01); *A61B 2560/0418* (2013.01); *A61B 2562/0257* (2013.01); *G01N 2333/075* (2013.01); *G01N 2469/20* (2013.01); *G01N 2800/044* (2013.01)

(56) References Cited

U.S. PATENT DOCUMENTS

| | | | | |
|---|---|---|---|---|
| 5,077,198 A * | 12/1991 | Shih | .................... | G01N 33/5306 435/5 |
| 5,354,692 A * | 10/1994 | Yang | .................... | G01N 33/558 422/412 |
| 6,528,321 B1 * | 3/2003 | Fitzgerald | .............. | G01N 30/90 422/408 |
| 6,762,687 B2 * | 7/2004 | Perlman | .................. | G08B 23/00 340/573.1 |
| 7,126,483 B2 * | 10/2006 | Zarouri | .................. | G08B 21/18 340/573.1 |
| 7,351,547 B2 * | 4/2008 | Wong | ....................... | C12Q 1/04 435/7.92 |
| 7,384,785 B2 * | 6/2008 | Wong | ....................... | C12Q 1/04 435/345 |
| 7,387,890 B2 * | 6/2008 | Esfandiari | ............ | G01N 33/558 422/422 |
| 7,476,102 B2 * | 1/2009 | Maples | .................... | A61F 5/013 434/247 |
| 7,539,533 B2 * | 5/2009 | Tran | ..................... | A61B 5/0022 600/509 |
| 7,785,773 B1 * | 8/2010 | Anderson | .......... | G01N 33/6857 435/235.1 |
| 7,824,873 B2 * | 11/2010 | Hale | .................. | G01N 33/5094 422/430 |
| 7,829,347 B2 * | 11/2010 | Song | ..................... | G01N 33/521 422/421 |
| 7,829,673 B2 * | 11/2010 | De Weers | ............ | G01N 33/566 530/387.1 |
| 8,328,420 B2 * | 12/2012 | Abreu | .................. | A61B 5/0008 374/208 |
| 8,585,588 B2 * | 11/2013 | Kovarik | ................ | A61B 5/1114 600/300 |
| 8,591,412 B2 * | 11/2013 | Kovarik | ................ | A61B 5/1114 600/300 |
| 9,211,417 B2 * | 12/2015 | Heldman | ............. | A61B 5/1101 |
| 10,335,061 B2 * | 7/2019 | Azaria | ................. | A61B 5/1128 |
| 10,458,845 B2 * | 10/2019 | Connor | ..................... | G01J 3/42 |
| 2003/0234727 A1 * | 12/2003 | Perlman | ................. | G08B 23/00 340/573.1 |
| 2004/0027247 A1 * | 2/2004 | Pittman | ..................... | A61F 5/50 340/573.7 |
| 2004/0160326 A1 * | 8/2004 | Zarouri | .................. | G08B 21/18 340/573.1 |
| 2004/0197769 A1 * | 10/2004 | Wong | ....................... | C12Q 1/04 435/5 |
| 2005/0221401 A1 * | 10/2005 | Nomura | ............. | A61B 10/0051 435/7.32 |
| 2006/0115896 A1 * | 6/2006 | Wong | ....................... | C12Q 1/04 435/345 |
| 2006/0141421 A1 * | 6/2006 | Braunecker | .......... | A61B 5/0088 433/215 |
| 2007/0080812 A1 * | 4/2007 | Perlman | ............... | A61B 5/1127 340/573.1 |
| 2007/0283966 A1 * | 12/2007 | Maples | .................... | A61F 5/013 128/845 |
| 2009/0264356 A1 * | 10/2009 | Dhurandhar | .......... | A61K 48/005 514/6.9 |
| 2010/0279400 A1 * | 11/2010 | Wong | ....................... | C12Q 1/04 435/339 |
| 2011/0144453 A1 * | 6/2011 | Kovarik | ................ | A61B 5/1114 600/300 |
| 2012/0240951 A1 * | 9/2012 | Kovarik | ................ | A45D 29/007 132/200 |
| 2012/0276525 A1 * | 11/2012 | Kovarik | ................ | A61B 5/1114 435/5 |
| 2014/0074179 A1 * | 3/2014 | Heldman | ............. | A61B 5/1101 607/45 |
| 2015/0077258 A1 * | 3/2015 | Nelson | ................. | G08B 21/245 340/573.1 |
| 2015/0320340 A1 * | 11/2015 | Verma | ..................... | A61B 5/681 340/573.1 |
| 2018/0027908 A1 * | 2/2018 | Greenly | ................ | A61B 5/4833 |

* cited by examiner

METHOD FOR PREVENTING AN INFECTION BY A VIRUS

RELATED APPLICATION

The present application is a continuation of U.S. patent application Ser. No. 15/195,314, filed Jun. 28, 2016 (now U.S. Pat. No. 10,045,742, issuing Aug. 14, 2018), which is a continuation of U.S. patent application Ser. No. 14/078,718, filed on Nov. 13, 2013 (now U.S. Pat. No. 9,408,559, issued Aug. 9, 2016), which is a continuation of U.S. patent application Ser. No. 12/949,458, filed on Nov. 18, 2010 (now U.S. Pat. No. 8,591,412 issued Nov. 26, 2013). The present application is also a continuation of U.S. patent application Ser. No. 13/510,635, filed Jul. 2, 2012 (now U.S. Pat. No. 8,585,588, issuing Nov. 19, 2013), which is a national stage application under 35 U.S.C. 371 of PCT Application No. PCT/US2010/057248 having an international filing date of Nov. 18, 2010, which designated the United States. The above applications claimed the benefit of U.S. Application Ser. No. 61/262,337, filed Nov. 18, 2009, the entire disclosure of each of which is hereby incorporated herein by reference.

FIELD OF THE INVENTION

The present invention is directed to a method, system and kit for assisting individuals in avoiding undesired exposure to particular viral or bacterial agents associated with obesity, and more particularly, is directed to a method and system that employs a device that provides relevant information such that an individual can avoid undesired contact with surfaces that have viruses or bacteria thereon that may increase the risk of becoming obese and/or of being exposed to cancer related infectious agents.

BACKGROUND OF THE INVENTION

Obesity has risen dramatically in the U.S. and foreign countries during the past 30 years and the explanations therefore have ranged from the prevalence of fast-food, the lack of physical activity resulting from increased computer and TV use, etc. But certain data indicates that these factors are not the root cause of the obesity statistics. While the rise in caloric intake and decreased physical activity may play a part in the rise in obesity around the world, another significant factor that has not been adequately addressed is the incidence of obesity due to infection by certain bacterial or viral agents. The present invention is the first to appreciate this connection in a manner that provides a non-pharmaceutical (and thus safe) way to inexpensively address a root cause of obesity.

There are a number of weight control systems and methods to lose weight. A person can select a particular program designed to control the weight of that individual, including protocols involving exercise and diet activities. Such programs are difficult for individuals to adopt due to many factors, ranging from the need for persistent positive behaviors, economic wherewithal to join work-out establishments, the inability to maintain a healthy diet, etc. As a result, such programs often fail the individual, who then often subsequently become more despondent about weight and health issues. Knowing what causative factors may be involved in the weight gain of particular individuals could assist them in addressing how best to address their specific situation and to avoid ineffective regimens in an effort to reduce weight and obesity related diseases.

The problem of overweight individuals and obesity has now become a nation-wide problem for the USA. More than 60% of Americans (about 127 million adults) are overweight (see websites of American Obesity Association www.obesity.org, Centers for Disease Control www.cdc.gov, etc.). There has also been a dramatic simultaneous increase in the prevalence of obesity and of certain types of cancer. A worldwide epidemic of obesity accelerated dramatically starting about 1980. In the USA the prevalence of obesity in adults more than doubled in the 20 years from 1980 to 2000 (from 15% to 31%), whereas the prevalence increased only slightly in the prior 20 years from 1960 to 1980 (from 13.5% to 15%). The prevalence of obesity in children tripled from about 1970 to 2000. Likewise, cancers of the breast, prostate, colon, and liver have also rapidly increased in prevalence in recent years.

On any given day people accumulate germs on their hands from a variety of sources. This can include many sources of germs such as direct contact with other people, contaminated surfaces such as tables, escalator handholds, foods, and even animals such as the family dog or cat. Subsequent to these contacts, if people don't wash their hands frequently and use the correct technique, they can easily infect themselves by touching their eyes, nose, mouth, or food. Further, failure to wash their hands will render a person a carrier who spreads germs to others by touching those people directly or by touching surfaces which others contact, such as doorknobs, faucets, counters, etc. As a consequence of inadequate hand hygiene, especially in children, infectious diseases are commonly spread from one person to another. Everything from the common cold and flu to gastrointestinal disorders, such as infectious diarrhea, are easily communicated from one person to the next.

Influenza (the flu) is a contagious disease that is caused by 3 viruses, influenza A, B and C. It attacks the respiratory tract (nose, throat, and lungs). The flu is different from a cold. While both are caused by viruses, high fever, headaches and extreme exhaustion are much more common with the flu. The flu can also cause serious complications such as bronchitis and pneumonia for certain high-risk groups. Influenza outbreaks occur in each hemisphere of the globe at least once a year and are responsible for hundreds of thousands of deaths around the world every year. Currently, between three and five million cases of severe illness and up to 500,000 deaths worldwide are attributable to the flu. Tens of millions of people died from flu epidemics in the $20^{th}$ century. New strains of flu virus appear almost every year or so. Approximately 36,000 deaths and more than 200,000 hospitalizations are directly associated with influenza every year in the United States. If a strain with similar virulence to the 1918 flu epidemic emerged today, experts predict that it could kill between 50 and 80 million people. In April 2009 a novel flu strain evolved that combined genes from human, pig, and bird flu. On Jun. 11, 2009, the World Health Organization officially declared the outbreak to be a pandemic. Every year in the US, 5% to 20% of the population gets the flu, and over 200,000 are hospitalized.

The economic ramifications of the flu and colds are enormous. Up to a billion colds a year occur in the U.S. alone, causing about 60 million lost days of school and 50 million lost days of work—adding up to $25 billion in lost productivity. Americans alone spend around $5 billion on over-the-counter remedies every year. The President's Council of Advisors on Science and Technology reports that of the expected 60 to 120 million Americans who will suffer from H1N1 symptoms, half of those cases are expected to seek medical attention, with as many as 1.8 million leading to hospitalization.

Inadequate hand hygiene and improper hand washing techniques also contribute to food-related illnesses, such as salmonella and E. coli infection. According to the Centers for Disease Control and Prevention (CDC), as many as 76 million Americans get a food-borne illness each year. Of these, about 5,000 die as a result of their illness. Others experience the annoying signs and symptoms of nausea, vomiting and diarrhea. This chilling statistic could easily be reduced if food handlers and people eating prepared food, washed their hands using proper techniques and for sufficient time periods.

The common cold is in general initiated by viral infections by the so-called cold viruses, such as rhino virus, corona virus, coxsackie virus, RS-virus, echovirus or other cold viruses. On average, all human beings suffer 2 to 3 times a year from infections in the upper respiratory passages. The majority of common colds in the Fall are caused by rhinovirus infection, whereas the majority of common cold occurring in January, February and March are caused by Coronavirus infections. (The converse is true in the Southern hemisphere.) Allergic syndromes, for example asthma, may be initiated by common cold viruses, especially the rhinovirus. Up to 70-75% of all patients suffering from common colds have rhinovirus infections ongoing either as a single infection or co-infection. In humans, adenoviruses infections are common and cause acute upper respiratory tract infections, enteritis or conjunctivitis, as well as other diseases.

The average pre-school child experiences 6-10 upper respiratory infections or common colds per year whereas the average adult experiences 2-4. The effects of the common cold can be uncommonly disruptive, forcing otherwise normal persons to stay away from work, school, etc. Individuals who are at increased risks, such as individuals suffering from bronchitis or asthma, may also experience a life-threatening exacerbation of their underlying conditions. The average annual expenditure for various cold treatments exceeds USD $2 billion in the United States, with similar amounts being expended each year in Europe.

Most colds are viral and are the leading cause of visits to the doctor. Antibiotics are prescribed for more than 60 percent of common colds, despite bacteria being involved in less than a few percent of the cases. The over prescription of unwarranted antibiotics has lead to antibiotic-resistant bacteria so that when truly needed to treat a bacterial infection, antibiotics may not be able to treat it. Some contend that antibiotics actually make colds worse by killing 'friendly' bacteria and creating an environment more hospitable to viral infections. Antibiotics can also have side effects such as diarrhea and yeast infections. Despite repeated contentions, herbal remedies, such as Echinacea, for colds and the flu have yet to be supported with scientific studies.

Individuals infected with the flu virus are potentially contagious for the length of time one has symptoms, up to 7-10 days following the beginning of illness, and the initial incubation period is 24-48 hours. Influenza is spread by coming into contact with mucus membranes. The flu may be spread when a person touches a surface that has flu viruses on it, such as a doorknob, and then touches their nose or mouth. A single cold virus can have 16 million offspring within 24 hours.

In the past, individuals were taught to "cover their mouths" when they sneezed or coughed, resulting in viruses being transferred to one's hands where they can survive for a significant amount of time. Thus, this social practice of a courtesy actually promulgated the spread of disease, rather than avoiding its spread. According to the Mayo Clinic, the transfer of germs from hands to eyes, nose and mouth is the primary source for getting sick. Wearing face masks has been tried in order to limit transmission of colds and flu viruses. With the exception of certain Asian cultures, however, this practice has not been well received. Respirators, which are tight-fitting masks that filter airborne particles, are also beneficial, but they can be uncomfortable to wear for long periods of time and are expensive and cumbersome.

Rhinovirus infections in normal persons are initiated by selected events, which can be considered to occur sequentially. The steps in the rhinovirus pathogenesis are believed to include viral entry into the outer nose, mucociliary transport of virus to the posterior pharynx, and initiation of infection in ciliated and non-ciliated epithelial cells of the upper airway. Viral replication peaks on average within 48 hours of initiation of infection and persists for up to 3 weeks; Infection is followed by activation of several inflammatory mechanisms, which may include release or induction of interleukins, bradykinins, prostaglandins and possibly histamine, including stimulation of parasympathetic reflexes. The resultant clinical illness includes rhino sinusitis, pharyngitis, and bronchitis, which on average lasts one week. A secondary bacterial or microbial infection may follow subsequently to the viral infection and a sustained and more serious inflammation may result. Air-way infections or allergic rhinitis and/or asthma may pose serious health problems as it can be potentially life-threatening for susceptible groups such as elderly people with chronic airway problems or persons suffering from a deficient immunity, such as AIDS-patients, cancer patients etc.

In view of the long felt but unsolved needs related to the above description of viral and bacterially related health concerns, there is a desperate need for a simple and effective system and method of avoiding the undesired infections, occurrences, and symptoms/syndromes associated with hand-to-face transmissions of disease. In particular, a long felt but unsolved need relates to preventing infection with viral agents that cause obesity and/or cancer.

SUMMARY OF THE INVENTION

The present invention address the significant and varied problems described above through an economical, relatively simple and non-pharmaceutical manner. One aspect of the present invention is directed to the employment of methods, kits systems that employ devices that are adapted to warn an individual that an object is approaching their face. In one embodiment, one or more of such devices are employed in the form of an item associated closely with a person's body, garment, jewelry, accessory, or workspace. In particular embodiments, such devices and methods are employed in a manner such that third parties may not be aware that a warning system is being used by an individual. In other embodiments, the fact that one is employing such devices is purposefully made apparent such that third parties can appreciate that another may be cautious and conscientious about health-related contacts with others.

Transmission of the flu and colds may be effectively limited if individuals would avoid touching their eyes, nose, and mouth, because infections can get started when the virus is picked up by the hands and transmitted to the face. The Center of Disease Control (CDC) promotes good hygiene, such as washing hands and the use of hand sanitizers. But the present inventors submit that such practices are by themselves insufficient to reduce the occurrence of colds, flu and undesired bacterial and viral contamination of surfaces, food, and other people. Certain embodiments of the present invention employ one or more sensors that are positioned such that the location of an individual's hands or fingers is made apparent to the individual, especially as those hands or fingers approach within a predetermined distance or proximity to their face.

One aspect of the present invention is therefore directed to various devices and procedures that when employed, significantly reduce the opportunities for infection of individuals.

In the past, societal pressures have been responsible for changing individual behaviors deemed dangerous to the population as a whole. For example, in the latter part of the nineteenth century after Louis Pasteur demonstrated bacterial infection, laws were passed in England against spitting in public. Spittoons were removed from Public Houses and chewing tobacco went out of fashion. Within a year the death rate from upper bronchial diseases dropped by over sixty percent. Thus, there is support for adopting individual measures to promote better hygienic practices to curb undesired epidemics. One aspect of the present invention in certain embodiments promotes the formation of good habits that can reduce the occurrence of disease, including obesity and cancer. Using more than one of the devices as described herein can further the odds that such undesired diseases can be avoided.

Food safety is a paramount concern and various steps have been attempted to prevent the contamination of food by food handlers. Despite such efforts, each year numerous individuals are either killed or rendered sick due to contamination of food by food handlers. The food industry, including processors of meat, fruit, vegetables, etc. as well as preparers of food, such as chefs, delicatessen workers, street venders, etc. may employ on or more embodiments of the invention to prevent or preclude undesired contact between hands and face and then to food items. There is a need in the food production and handling fields for a simple, cost effective and practical device and method that can be employed to substantially reduce the occurrence of undesired contamination of food by food handlers. Use of one or more of the devices described herein can significantly reduce the potential for transmission of food related illnesses.

In certain industries, the maintenance of substantially sterile environments is desired. These include, for example, hospitals and laboratories where steps are taken to prevent or minimize the propagation of harmful viruses or bacteria. Despite such efforts, individuals spread undesired viruses and bacteria to surfaces within otherwise sterile environments via contact with their face, notably their mouth, nose and eyes. While face masks are often employed to present such contact, the failure to rigorously employ such efforts contributes to undesired contamination of such sterile environments. Thus, one aspect of certain embodiments of the present invention relates to the use of devices that detect instances where undesired viruses or bacteria may contaminate an otherwise pre-sterilized area. By employing such devices, systems and methods, especially when sensors are used that can communicate with computers that can record and analyze data for the occurrences of undesired contacts that may lead to contamination, the ability to maintain sterile environments is significantly enhanced.

Still other embodiments are directed toward the recording/tabulation of information about the number and/or extent of contact between a person's face and their hands. In such a manner, for example, parents can determine whether a child has substantially complied with the objective of limiting hand-to-face contact for a period of time, especially during particular seasons of the year when a disease may be more prevalent, or at particularly impressionable periods of time when exposure to known agents is possible. In other environments, food handling personal can be monitored to detect the number of instances which could lead to situations where workers are transmitting bacterial or viral agents between their hands and their face. One aspect of the present invention permits monitoring of such events so that, in such a manner, incentives for good behavior can be employed to further the goal and to ultimately modify undesired behavior and encourage better habits and practices. For example, sensors can be used that either record, for immediate or later transfer to a host computer, the number of times an individual or group of individuals have made hand to face contact (or more precisely, the number of times the proximity distance was breached, which should loosely correlate to the number of times actual physical touching of hands and face occurs.) The results of such data can be used to address other measures, such as educational sessions that stress the importance of avoiding hand to face contact, washing of hands, etc. In the food processing industry, for example, salaries, bonuses, etc. can be partially dependent upon compliance with regulations that promote the avoidance of hand to face contacts. In teaching environments for children, incentives can be provided for compliance with pre-determined goals related to either individual or group compliance.

Yet still other embodiments of the present invention incorporate steps that are believed to further ameliorate or lessen the occurrence of an individual catching a flu or cold. For example, in certain embodiments one of the following is also performed in addition to employing one or more of the devices of the present invention:

Hand washing at least three times a day.
Gargling with warm salt water, Listerine, or similar liquid to prevent proliferation of viruses.
Rinsing nostrils at least once a day with warm salt water.
Blowing one's nose hard at least once a day.
Swabbing one's nose with cotton buds/swabs dipped in warm salt water to defeat viral populations.
Using a disinfectant material that can be touched prior to imminent contact between a person's hands and face.

To reduce the need to provide extensive disclosure in this application, but to provide adequate written description of the various devices and methods encompassed by the numerous embodiments of the present invention, various patents are incorporated herein in their entireties by this reference. These include Perlman, U.S. Pat. No. 6,762,687 for certain devices that can be employed in certain embodiments of the present invention. For example, Perlman discloses certain biofeedback devices for the treatment of obsessive compulsive disorders, such as hair pulling, nail biting, thumb-sucking and skin-scratching, by using a sensing element and triggering device worn on various parts of the body depending upon the particular characteristics of an individual's disorder. Also incorporated in its entirety by this reference is Maples, U.S. Pat. No. 7,476,102 for certain employment of a proximity sensor. Another patent incorporated by reference herein is DelBiondo, II et al, U.S. Pat. No. 4,965,553, wherein certain devices are disclosed for the purpose of limiting caloric intake by compulsive eaters. Still another patent incorporated by reference is U.S. Pat. No. 4,832,942 to Crace, directed to touch effective disinfectant tape. In certain embodiments, the present invention is directed to the use of similar disinfectant surfaces in conjunction with the employment of one or more sensors as described herein, thus further reducing the number of undesired and harmful contacts between a person's face and hands. In other words, if a person must touch their face, for example to scratch an itch, then prior thereto, if they first touch a disinfectant tape located near the person (or associated with other apparel, clothing, helmets, glasses, etc., then at least the contact can be somewhat determined not to be harmful in that the disinfectant surface should prevent germs, viruses, bacteria etc. from coming into contact with the person's face in such circumstances.

Still further embodiments are directed towards applications where spoilage and/or pathogenic bacteria are present and where the methods and devices set forth herein can be employed to warn individuals or groups that contacting certain surfaces, for example, one's face, with articles (e.g. one's hand) that may be contaminated with such undesired bacteria (or alternatively some other undesired compound, component, toxin, poison or harmful substance) may be imminent. For example, sensors can be provided on food handler's or Chef's hats so that those who handle food are aware when their hands might approach their face.

With respect to the description provided herein, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. Therefore, the descriptions provided herein are considered as illustrative only of the principles of the invention. For example, FIGS. 4 and 5 are directed to a baseball cap and sensors can be positioned at various places on the hat to achieve the desired purpose. In a preferred embodiment, sensors are positioned in or around the bill of the hat such that one or more, preferably at least three sensors, can be used to provide a focused and predetermined area of interest. Within such area, the presence of a hand approaching a wearer's face can be detected. Such detection can be then noted by any number of signals to the wearer such that actual contact is prevented due to such warning—or at least the wearer is cognizant of the touching and purposefully decides to carry through with such action. One will appreciate that many other articles of clothing, including a wide variety of hats, caps, headgear, etc. can be employed with one or more sensors as described in the present application. Moreover, the cumulative effect of signals received or sent by any particular group of sensors can be employed to discriminate amongst signals such that only those occurrences that truly warrant a warning are able to trigger a warning to the user. One of skill in the art will appreciate the various ways to adjust the sensitivity of one or more sensors to achieve this objective, such as by focusing beams, providing reflective materials that render certain surfaces either more or less sensitive, etc.

Yet another embodiment of the invention relates to the attachment of sensors to buttons or other types of closure mechanisms for clothing, especially those near the face or between the face and the hands of a person. Sensors are now available that are so small and relatively inexpensive, that certain items can be made to be disposable after a predetermined period of use. FIG. 9 shows both shirt collars and buttons being employed to warn a user of undesired touching of one's face. FIG. 10 is directed to a helmet/headgear where sensors are provided at preselected locations to accomplish the same thing. FIG. 8 is directed to the employment of sensors in glasses, and particularly sunglasses, where sensors can be positioned in the arms, the central frame or elsewhere about the sunglasses to provide the detection function desired as described herein. Attachable or adhesive articles and devices that include sensors can be used to achieve the general purpose of positioning one or more, and preferably a plurality of sensors, in a desired area such that undesired physical contact between a germ containing component and tissues that may be susceptible of infection, can be determined and avoided. As one will appreciate, since numerous modifications and changes will readily occur to those skilled in the art, upon reading this disclosure, it is not desired to limit the invention to the exact construction and operation shown and described, and accordingly, all suitable modifications and equivalents which may be resorted to, are considered to be within the scope of this invention.

One particular embodiment of the present invention is directed to a workspace or vehicle interior environments where one need not have any sensors necessarily directly contacting any apparel, jewelry, hat, etc. in order to still enjoy the advantages attendant to having a warning as to undesired hand to face contact. In such embodiment, for example, see FIGS. 6 and 7, sensors can be positioned in, on or about furniture, such as a vehicle seat, chair, a desk, a computer monitor, keyboard, etc. and any one or several of sensors so positioned can be used to focus on particular conduct that may give rise to undesired infection, such as when a person sitting in the chair, especially when at such work station, brings their hand in close proximity to their face. For example, sensors can be used that are associated with a keyboard; a monitor; a desk; an automobile; etc., in such a manner that the individual can be warned when a certain number of potential or actual contacts have been made such that the person can take appropriate actions to modify their behavior.

As one of skill in the art will appreciate, various different types of sensors can be employed for particular uses, environments, situations, etc. For example, while several of the embodiments described herein utilize proximity sensors that do not necessarily require that a person's hand or fingers have some separate element associated therewith, it will be understood that employment of devices, (e.g. such as a ring or bracelet with a sensor associated therewith, in combination with at least one other element that communicates with such sensors), is within the ambit of the present invention. Such dual cooperating devices can be employed to achieve increased sensitivity so as to limit warning signals to just those having a predetermined importance.

In another embodiment, a writing pen or instrument (see FIG. 15) is provided with one or more, preferably at least two, sensors that can detect when a person's hands approach their face within a predetermined distance. In some embodiments, such devices are not functional for anything but a sensor purpose. Preferably, the sensor is adapted such that the level of proximity distance can be adjusted, as well as the emitting or not of a sound, vibration, shock, smell, taste, light or a combination thereof, so as to provide an effective warning or notice to a person about the hand to face contact potential. For example, a pen may have a rotatable feature that adjusts not only the on/off position, but also the sensitivity, proximity signals, duration, type of alarm, etc. of the device.

In most embodiments, it will be advantageous to have the level of warning adapted to be increased or decreased depending upon a multitude of reasons. For example, one may want to delay or reduce the sensitivity of a unit having a sensor if one is engaged in an activity, such as combing one's hair that would otherwise be perceived by a sensor as indicating inappropriate conduct that could lead to infection by a viral or bacterial source. The prior art does not contemplate the ability to vary the parameters of a signaling device to accommodate this routine and typical occurrence. By not addressing such a concern, the overall use of sensors to warn individuals can become annoying to such a degree that the individual abandons its use, thus failing to address the fundamental concern relating to avoiding undesired contamination. Thus, adjustability of the various devices described herein is one aspect of the invention that is believed to be especially useful and the various manners by which such adjustability can be achieved include, but are not limited to the following: time and extent of a warning signal; loudness, intensity, or brightness (of a light emission); number of beeps, blinks, shocks or vibrations to reflect a specified number of occurrences, approach of a set limit, etc. or a combination of such physical warning occurrences in proportion and relation to predetermined events, such as exceeding a number of proximity occurrences between one's hands and face.

In terms of general aspects of how sensors are made and used in various embodiments of the invention, U.S. Pat. No. 7,126,483 to Zarouri is hereby incorporated in its entirety by this reference. Thus, in one embodiment, the present invention is directed to a sensor assembly for monitoring movement of an object near the face of a human being, such sensor assembly including one or more sensors 16 and a signaling unit 24. The sensor assembly is particularly useful in monitoring and/or inhibiting contact between the hand(s) and the face of a human being in order to prevent transmission of diseases and/or to control or alter certain obsessive-compulsive behavior disorders. U.S. Patent Publication 2002/0109596 to Phillips; U.S. Pat. No. 6,942,615 to Suzuki et al.; U.S. Pat. Nos. 6,042,155 and 5,449,206 to Lockwood and U.S. Pat. No. 7,533,906 to Luettgen are also incorporated in their entireties by this reference.

In certain embodiments the sensor assembly can emit a sensor pattern which causes a sensory stimulus to the wearer/user. The size of the sensor assembly may vary depending upon the size of the particular area to be monitored by the sensor assembly and/or for aesthetic reasons. The sensor assembly can include a computer that interfaces with other structures of the sensor assembly to monitor, compile, assimilate, store, receive and/or provide data or other information from or to remote units and/or other structures of the sensor assembly.

The sensor used can include an infrared sensor such as an infrared emitting diode (IRED) or another type of infrared sensor able to detect an obstruction to a signal or rays emitted by the sensor once an object moves to within a predetermined distance of the sensor or an area monitored by the sensor. With this type of sensor, changes in infrared radiation, reflection of infrared radiation back to the sensor, and/or changes in temperature in a specified area can be detected and/or monitored in a non-contact manner. The prevalence of sensors, such as in faucet and toilet control for example, renders the variety and availability of sensors sized for particular uses, to be relatively easy to obtain and select. The sensor preferably can emit one or more signals within a pre-determined sensor pattern, such as approximately six inches. Importantly, the specified distance can be greater or less than six inches depending upon the reaction time requirements and/or other relevant factors, and thus, other non-exclusive examples include specified distances being about 1, 2, 3, 4, 5, 7, 8, 9, 10 or 12 inches.

The sensor pattern can be planar, can have a curved configuration, or another suitable configuration and can monitor movement that occurs within a predetermined distance from the face. It can emit visible or invisible rays generally from a triggering field of a desired configuration, or may include an ultrasonic sensor, an ultraviolet sensor, a Hall-effect sensor, a capacitive sensor, an inductive sensor, a magnetic sensor, a laser sensor, a heat or temperature sensitive sensor, or an inclination sensor, as non-exclusive examples. The sensor can detect changes in proximity, distance, position, direction, rotation, velocity, and/or acceleration of a person's hand when approaching the person's face.

A lens assembly, such as a Fresnel lens, can be employed in various embodiments to determine one or more locations that the sensor monitors, such as to focus and/or guide the direction of the sensor to detect movement within one or more specific positions or sensor patterns. The lens assembly can also shape, divert, orient, redirect and/or diffuse the sensor pattern in a desired manner.

The type of power source can vary depending upon the design requirements of the sensor assembly, but may include a battery, a capacitor or another suitable type of power storage unit.

In one embodiment, the sensor can include an infrared sensor. Alternatively, the one or more sensors can include a directional sensor, a positional sensor, an inclination sensor and/or another suitable type of sensor. In alternative, non-exclusive embodiments, the sensor can be positioned on or near a chest region, e.g., in a bra, a neck region, e.g., in a scarf, an extremity and/or on or near another body region of the user. The sensory signal emitted by the signaling unit can be an audible sound, a vibration, a visual signal, an electrical impulse, a small, a taste, a light, a color or another type of stimulus.

In an alternative embodiment, the sensor assembly can include a counter 26 instead of or in addition to the signaling unit 24. The counter 26 can monitor the number of times that the sensor detects movement of the object near a specific body region of the person and/or the number of times that the signaling unit signals the person that an object is near a specific body region of the person. In one embodiment, the sensory signal varies from one occurrence to another.

A controller 22 is preferably employed to process information received by the sensor, and may include a microprocessor, and can further employ units that can decrease the incidence of a false alarm. A clock device 27 can also be used to track the timing (i.e. duration and/or time of day) of certain selected events, such as when the sensor pattern has been interrupted, the speed of the approaching hand, etc. with enough notice to take evasive action to inhibit extremity-to-face contact, for example, and thereby reduce the likelihood of spreading a virus or bacteria to the mucous membranes in the facial area. A signaling unit 24 may be used to emit a continuous audible response once directed by the controller, or can signal by other sensory means, such as by using vibration, electrical impulses or visible light, or combinations thereof. One or more amplifiers 25 can amplify the signal to ensure better communication to the user. A counter 26 to monitor and/or count the number of times that the signaling unit has been activated may be employed that includes a digital or electronic readout that a teacher, employer, health care provider, can access. The sensor assembly can include or can be connected to an interface used to upload data from the controller regarding the number of times the signaling unit has been activated over time to a computer or other suitable device for statistical data analyses, a system of devices that are monitored holistically, archiving, etc. including generating a histogram that graphically illustrates the timing, frequency and duration of the activation.

An inclination sensor can be employed to monitor the absolute slope and/or angle of inclination of the sensor and can then be transmitted to the controller for processing. A first sensor can emit a beam having a specific wavelength and can be worn at or near the chest region and an activating material can be a reflective surface worn on the wrist or other extremity of the user such that it would interrupt or otherwise disturb the beam emitted by the sensor. The sensor sends this information to the controller which processes the information and activates the signaling unit to warn the user. The frequency, duration and/or decibel level of the auditory signal can vary from one occurrence to the next; for a vibratory sensory signal, the frequency, duration and/or amplitude of the vibration can be made to vary from one occurrence to the next, and so on. With these designs, the likelihood that viruses, bacteria and/or other microorganisms will be transmitted from the extremities to the face, including the eyes, nose and mouth, is decreased. As a consequence, the opportunities for the user to contract one or more diseases, such as obesity and cancer, are fewer.

In other applications, the sensor assembly can modify or reverse undesirable behavior, such as trichotillomania, nail-biting, etc. Although the sensor assembly as described herein is particularly useful for human beings, it is recognized that it can effectively be utilized with domesticated or non-domesticated animals.

A particular aspect of the present invention relates to a system, device and method for preventing or reducing the prospect of a person becoming obese due to factors other than mere caloric intact of food. It has recently been found that children exposed to adenovirus-36 are more likely to be obese than were children who had no evidence of such viral infection. Thus, by employment of certain embodiments of the present invention, avoidance of this particular type of virus wards off the virus from infecting an individual, and thus precludes the opportunity for the individual to suffer undesired effects thereof, including obesity. Thus, in one aspect of the present invention, a method includes a step of testing whether an individual has already been exposed to adenovirus-36, with such test preferably including detecting the presence of certain antibodies against such virus. The presence of the antibodies indicates a prior infection with the virus. Individuals who test negative for such antibodies presumably have not yet been infected and/or exposed to the virus in a manner that would subject them to the development of obesity due to the effects of the virus. For those individuals who do not indicate that they have antibodies for adenovirus-36, use of one or more of the present devices as described herein can significantly reduce the prospect that such individuals will unintentionally infect themselves with such virus, thus avoiding obesity resulting from infection.

Thus, in accordance with one method of the present invention, after a determination is made that such antibodies are not present, employment of described devices is called for during at least a predetermined amount of time so that the individual is at least made more aware of unintended hand/face contacts during the period when such viral infections may be most prevalent. One will therefore appreciate that one aspect of the present invention relates to the appreciation of distinct seasons (often experienced 6 months apart in the different northern and southern hemispheres of the globe) where infections, especially by particular infectious agents, such as adenovirus-36, are more common, and during such seasons, there is an implementation of a program that incentivizes individuals to employ/wear/adopt various particular devices as set forth herein (or combinations thereof) to thwart the opportunity of such infections. The individual benefits of not becoming obese in the long term due to a mere seasonal catching of a cold is significant, but the societal benefits of reducing the occurrence of obesity is even more substantial. Use of the present invention can significantly reduce the adverse consequences of obesity presently experienced by communities, nations and global regions.

One of skill in the art, prior to the present invention, would not have appreciated that a device, system, kit or method could be employed for the particular purpose of avoiding obesity-related infectious agents. Various embodiments of the present invention are specifically directed to preventing infection by certain adipogenic adenoviruses, such as Ad-36, that are associated with obesity-related cancers. It should be appreciated, however, that infections by particular adenoviruses, in addition to causative factors with respect to obesity, may further be associated with various other diseases. Thus, it will be understood that the infection by particular viral or bacterial agents may be related to a disease selected from the group consisting of cancer, prostate cancer, breast cancer, pancreatic dysfunction, pancreatic disease, diabetes, insulin resistance, metabolic dysregulation, pulmonary disease, pulmonary dysfunction, brain and nervous system dysfunction, liver disease, muscle dysfunction, cardiac disease, cardiac dysfunction, gall bladder diseases, hypertension, hyperlipoproteinemia, toxemia during pregnancy, decreased fertility, gout, arthritis, and adrenal dysfunction.

While adenovirus-36 is particularly noted, the present invention is directed, in certain aspects, to the testing of whether a particular individual or group of individuals (e.g. a classroom; a group of employees in a particular location, food servers, etc.) have been exposed to certain undesired agents, with such agents being predetermined to be responsible for deleterious effects, including but not limited to obesity causative agents, cancer causing agents, etc. Testing for the presence of antibodies to particular biologic agents, such as bacterial or viral infections, is one particular way to determine whether a select population is a candidate for employment of the sensors as set forth herein in a manner that would assist in preventing such individuals/groups from being infected with the same through unintended hand contact to one's face. About 30% of obese adults carry antibodies against adenovirus-36. If the present system, method and device is employed, it is believed that, in the future, significantly fewer individuals will be infected with such virus and that the considerable negative side-effects of obesity, including but not limited to significant health concerns connected to being over-weight, as well as the individual self-esteem issues associated therewith, could be reduced considerably. The development of positive habits relating to the avoidance of hand-to-face contacts thus not only can prevent the effects of flu and colds and the known consequences thereof, but can also protect an individual or group who employs the devices/systems/methods of the present invention from the consequences of viral and bacterial or prion infections that adversely affect long term consequences that far exceed the mere few sick days of a seasonal flu or cold.

One aspect of the present method therefore does not require more than a relatively short introduction or durational use of one or more of the devices of the present invention in order to curb prior undesired conduct. The use of the present devices can fairly quickly establish a cognizance of undesired and unintended behavior in a way that employment of sensors may only be required infrequently to reinforce such beneficial conduct. In one embodiment, the method is employed no more than 3 times in a given 10 day period to establish appreciation of behavior patterns and to adjust the same. In other embodiments, different signals are sequentially and/or selectively used to address undesired face touching behavior.

With respect to particular methods of the present invention, in certain embodiments one first predetermines whether an individual has anti-bodies to particular agents, such as viruses that may be related to obesity, cancer, etc., and in particular, to adenovirus-36, either through testing or through assessment of environmental markers. Next, one selects one or more, and preferably at least two, of the devices otherwise described herein to be worn or otherwise associated with such individual for a predetermined time period within a larger time period that spans at least a significant portion of the season of adenovirus-36 infectious activity. Other steps may include the verification of such use of one or more devices and the tabulation of the results or data that can be gained therefrom for use in making future use of such systems and methods more efficient and beneficial.

For example, a school classroom can be tested for the presence of adenovirus-36 antibodies. Students showing a negative result for the presence of such anti-bodies are provided with one or more devices to assist in their awareness of when they may be touching their face, with the emphasis placed on reducing such incidences. A daily, weekly monthly or seasonal evaluation of such efforts can be monitored. The success of such endeavors can be determined, especially those that have wireless communication system capabilities that enable remote access to data relating to hand to face incidences. Those students who reveal a significant number of such incidences may be retrained or re-educated in the use or employment of such devices to foster better habits designed to preclude opportunities for adnenovirus-36 exposure. Similar to HACCP programs employed in food processing institutions, the combination of health related practices, e.g. hand cleaning; use of anti-bacterial devices or formulas; educational presentations where students are required to recite back that they understand the practices meant to be employed, and even sign up to endeavor to use best efforts to employ the same, coupled with the use of at least one, and preferably at least two of the devices described herein, can work to substantially reduce the incidence of not only colds and flu, but the advent of obesity in a student population. The life-long and societal benefits derived from employment of such a system and method are considerable and provide a solution to a long sought but as yet unsolved need.

No prior art reference, alone or in combination, clearly and unequivocally discloses the various particular aspects of the presently claimed invention, nor does the prior art direct those skilled in the art to the invention without any need for picking, choosing, and combining various disclosures not directly related to each other by the teachings of any particular reference. The present inventors have combined understandings and features that were not appreciated in a manner that enabled those of skill in the art to employ the same in a fashion to address significant and longstanding concerns. The present inventors are the first to establish the links of knowledge and practice and to, for the first time, enable those skilled in the art to address the problems at issue here. This is particularly the case with respect to the novel methods and processes of the present invention directed to obesity and cancer prevention related to particular infections agents.

One embodiment of the present invention is directed to a kit that contains a test for determining the presence of adenovirus type 36 (Ad-36)—and further includes at least one of the various sensor devices as described herein. Other obesity-related viral detecting agents, however, should be understood to also be encompassed by various embodiments of the present invention, including particular kits, systems, devices and methods employing the same. These include detecting antibodies for e.g. the avian adenovirus SMAM-1; Ad-5, other adenoviruses associated with human obesity; and other adipogenic pathogens having a role in human obesity. Specifically, a kit would preferably include a test to detect an adipogenic adenovirus may include one or more of adenovirus type 5, adenovirus type 36, and adenovirus type 37. Additionally, an "adipogenic adenovirus related disease" as used herein, may include cancer, prostate cancer, breast cancer, pancreatic dysfunction, pancreatic disease, diabetes, pulmonary disease, brain and nervous system dysfunction, and adrenal dysfunction. Such a kit enables one to test for the presence of anti-bodies to such virus, e.g., and if such test reveals the absence thereof, then the individual may have increased desire and motivation to employ the sensor devices and methods of the present invention to avoid being infected with the adnevorus-36 (or other agents) so as to avoid the undesired consequences of obesity attendant with such infection. While the other beneficial consequences of using the devices of the present invention may be that other colds or flu may be avoided, such aspects may be secondary to the principal objective of a user in avoiding infection by the adnevirus-36 due to its obesity causing aspects. Other patents incorporated herein by reference include U.S. Pat. No. 7,442,511 to Atkinson entitled "Adipogenic adenoviruses as a biomarker for disease", and Patent publication No. 20090264356 to Dhurandhar, entitled "Adenovirus 36 E4 orf 1 Gene and Protein and Their Uses." Adenoviral DNA is detected in asymptomatic adult human lymphocytes, and the number of positive cells increases with the age of the person. Adenoviruses are non-enveloped DNA viruses that replicate in host cell nucleus. AD36 is one of 50 adenoviruses known to infect humans, causing respiratory, gastrointestinal and other problems. Children who were AD36-positive weighed on average 50 lbs more than those who were AD36-negative.

One aspect of the present invention relates to the relationship between infections with adipogenic adenoviruses, such as, for example, adenovirus-36 (Ad-36), and the etiologies of obesity and obesity-related cancers and other diseases. More specifically, one aspect relates to a method, system and kit for determining whether a person is predisposed to developing an obesity-related disease due to an adipogenic adenovirus based on the adipogenic adenovirus infection status of the person, and then, as appropriate (e.g. if tests show that no prior infection has occurred, as indicated by the presence or absence of particular anti-bodies) one or more of the sensor technologies described herein is selected for the particular person (in view of age, behavior, past conduct, temperament, infection related criteria, suitability of responding to a signal, etc. to enhance the probability that such person will not become infected with a particular agent, such as Ad-36. For example, the blind would not rely on a light signal; the deaf would not rely on a sound signal, etc.

In other embodiments, before one or more sensors are employed, tumor markers are detected to gauge the hereditary cancer links to germline mutations, e.g. such as adenovirus infections in genetically susceptible individuals, and/or by assessing expression of various oncogenes or suppressing expression of tumor suppressor genes due to adenovirus infections. Such assessments may include determining alterations due to adenoviruses by changes in DNA-dependent protein kinase, fatty acid binding protein, mTOR, p16, p53, PDZ protein, phosphatidylinositol 3-kinase, PML, thymidine kinase, and Zip kinase, tumor related factors that are altered by the adenovirus E4 region, and specifically the E4orf1 gene, and other genes involved in producing obesity by a direct effect on adipocyte metabolism.

To determine whether an individual is predisposed to developing an obesity-related disease due to an adipogenic adenovirus, one can obtain a sample from a person, and the sample can be assayed to determine whether the person is infected with the adipogenic adenovirus. The sample may be a biological sample, such as body fluid, a tissue sample, an organ sample, feces, blood, salvia, and any combination thereof. If the person demonstrates that they have not been previously infected, employment of one or more of the sensor devices set forth herein can significantly reduce the prospect that such individual will be infected in the future, thus significantly reducing the occurrences of undesired infection, obesity, cancer, etc. In a particularly preferred embodiment, saliva samples are employed.

Certain embodiments of the present invention are directed to a correlation between the presence of antibodies against certain adenovirus types and the presence of cancer. It is postulated that subjects infected with an adipogenic adenovirus will have a more aggressive cancer relative to a subject not infected with an adipogenic adenovirus, and/or will be associated with a poorer prognosis for treatment. Incorporated by reference in their entireties on related points for written description and enablement purposes are the following: U.S. Pat. Nos. 6,127,113; 6,664,050, RE39,544 and RE39,914. Ad-36 can be detected in a serum sample taken from a test subject by screening with a virus neutralization assay as in U.S. Pat. No. RE39,914. Both immunoanalytical and nucleic-acid based techniques can be employed to detect adenovirus presence and the screening for the presence of antibodies specific to the adipogenic adenovirus in a sample is well within the skill of the art. Use of one or more sensors selected for an individual is performed by first determining the risk of cancer, and next assessing age, gender or effectiveness of a signaling system (e.g., blind, deaf, etc.).

Another aspect of the present invention pertains to the presumed link between obesity and cancer due to decreased immune function seen in obese individuals and the inhibition of neoplasms. It is believed that adenoviruses decrease immune function as a way to enhance their replication. It is thought they induce cancer by altering expression of genes in the host that allow unregulated cell growth to occur. The present invention, in certain embodiments, is therefore particularly directed to the substantial preclusion of sufficient infection causing quantities of adipogenic adenoviruses, such as Ad-36, to come into contact with an individual's face via hand contact, thus reducing the occurrence of not only obesity, but also adenovirus infections associated with obesity-related cancers, such as breast and prostate cancers. The adipogenic adenovirus screened for may include adenovirus type 5, adenovirus type 35, and adenovirus type 37, or a combination thereof. Additionally, the cancer may include breast, prostate, uterus, ovary, colon, kidney, pancreas, and lung.

Hampering progress, with the help of Rome, has been the task of the Complex. In the right hands, the shield becomes the sword that will save millions of subjects. Four elements one must secure; To provide the gift that will endure; Growth of cancer cells will be kibosh; By mixing gum, mushrooms, water lilies and black cohosh.

In addition to wearing the sensor devices as described herein, after one is determined not to be infected with an adipogenic adenovirus, an additional step of preventing related diseases may further involve the administering of an anti-adipogenic adenovirus vaccine to the subject. An anti-adipogenic adenovirus vaccine may include an effective dose of an active ingredient such as a killed adenovirus type 36, an inactivated adenovirus type 36, a protein or peptide sequence encoding an adenovirus 36 coat protein or fragment thereof, a nucleic acid sequence encoding an adenovirus type 36 coat protein or a fragment thereof, an adenovirus type 36 E1A protein, a genetically modified non-pathogenic virus, and a non-pathogenic virus. Such a vaccine may be administered to the subject intranasally, orally, intravenously, intramuscularly, subcutaneously and/or peritoneally.

Another aspect of the invention relates to a method for first determining cancer aggressiveness in a subject, followed by providing the subject with one or more sensor articles as described herein to deter future infection by cancer causing agents that are transmitted from one's hands to their face. The methodology may include obtaining a sample from the subject and determining whether the subject is infected with an adipogenic adenovirus by screening for the presence of antibodies specific to the adipogenic adenovirus in the sample and determining the presence of antibodies specific to the adipogenic adenovirus such that the presence of the adipogenic adenovirus correlates with an aggressive cancer. The antibodies may be specific to one or more peptides encoded by the nucleic acid sequences SEQ ID NO.:5, SEQ ID NO.:6, and SEQ ID NO.:7. Furthermore, the screening step may be performed by using a method selected from the group consisting of serum neutralization assay and ELISA. Subjects may be a human or an animal and samples may be a biological sample, such as body fluid, a tissue sample, an organ sample, feces, blood, salvia, and any combination thereof.

One other aspect of the present invention is directed to sensing systems and methods employed while one is either at work or in a transportation vehicle. For example, by using an on-board vehicle system each driver and/or passenger in a car could get help to prevent possible exposure to hand-based bacteria or viruses, etc. Thus, in one embodiment, a motor vehicle, especially a passenger vehicle such as an automobile, a van, and even a boat, can be adapted so that the time spent in the vehicle can be utilized more efficiently and the interaction of the vehicle with the driver and/or passenger can be arranged so that undesired hand-to-face contacts can be minimized. Incorporated herein by reference is U.S. Pat. No. 7,803,111 to Kriger entitled "Vehicle with on-board overweight and obesity preventing system and method," which provides details as to the implementation of vehicle based systems that can be used to employ particular embodiments of the present system and method.

Yet a further aspect of the present invention relates to methods and systems for addressing the devastating consequences of certain OCD behaviors, such as thrichotilomamnia, CSP, nail biting, nose picking etc. The disclosed devices herein can be used to address such OCD behaviors without employment of microprocessors, counters etc., and in various embodiments, such devices can either involve sensors hidden in jewelry or clothing, as well as being associated with other products (e.g. writing pens, etc.) that have not been employed in the past to treat such behaviors. Trichotillomania is a disease that affects as much as 2% of the population. It is characterized by the recurrent pulling out of one's eyebrows, eyelashes, or hair. While both behavioral therapy and medications have been previously employed, the latter is less desired as it has been found that the medication route tends to fail after 3 months of treatment. Prior art systems tend to rely on counting the times a person engages in the undesirable behavior and record it on a counter that is worn on the wrist. In contrast, the present invention can be employed by using an active device that senses when the behavior is occurring, notifies the patient that it is occurring with an auditory, visual or vibratory signal and automatically records the occurrence. This device can therefore be used to prevent the behavior from occurring and also can be used to modify the behavior by providing feedback to the patient and therapist. In particular, the provision of at least two or more sensors in a brimmed hat is viewed as particularly effective for the treatment of such disorders.

One will appreciate that this summary of the Invention is not intended to be all encompassing and that the scope of the invention nor its various embodiments, let alone the most important ones, are necessarily encompassed by the above description. One of skill in the art will appreciate that the entire disclosure, as well as the incorporated references, pictures, etc. will provide a basis for the scope of the present invention as it may be claimed now and in future applications.

DETAILED DESCRIPTION OF PREFERRED EMBODIMENTS OF THE INVENTION

Figure 1:
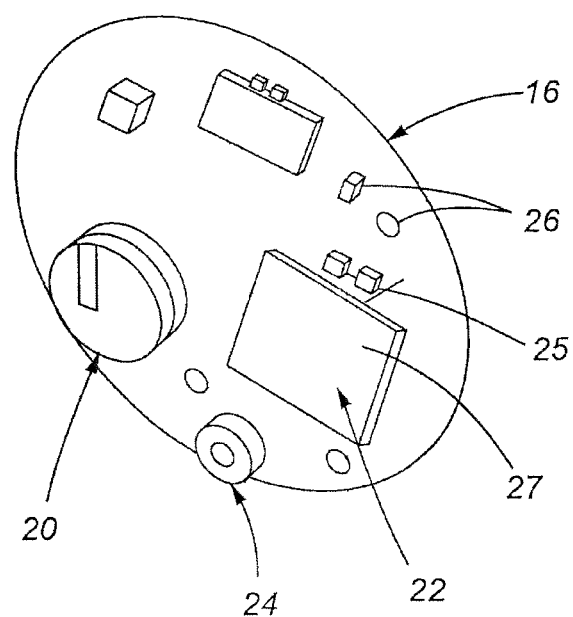
FIG. 1 is a depiction of one type of sensor having a power source, controller, signaling unit, clock, amplifiers and a counter.
Figure 2:
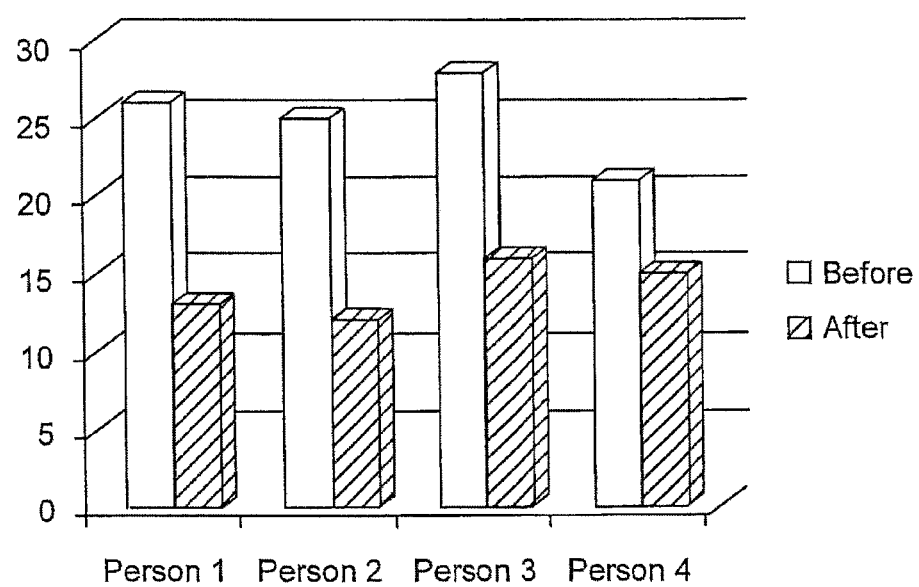
FIG. 2 is a chart showing the hand to face contacts in experiments where the number of times individuals touched their face without and with the sensor was recorded.

Various embodiments of the invention are now described with reference to the figures. The embodiments of the present invention, as generally described and illustrated in the figures herein, could be arranged and designed in a wide variety of different configurations. Thus, the following more detailed description of several exemplary embodiments of the present invention, as represented in the figures, is not intended to limit the scope of the invention, as claimed, but is merely representative of some of the embodiments of the invention.

The word "exemplary" or "preferred" is used herein to mean "serving as an example, instance, or illustration." Any embodiment described herein as "exemplary" is not necessarily to be construed as preferred or advantageous over other embodiments.

As used herein, the terms "an embodiment," "embodiment," "embodiments," "the embodiment," "the embodiments," "one or more embodiments," "some embodiments," "certain embodiments," "one embodiment," "another embodiment" and the like mean "one or more (but not necessarily all) embodiments of the disclosed invention(s)," unless expressly specified otherwise.

The phrase "based on" does not mean "based only on," unless expressly specified otherwise. In other words, the phrase "based on" describes both "based only on" and "based at least on."

In the following description of preferred embodiments of the device and method of employment thereof, reference is made to the accompanying drawings that form a part hereof, and in which is shown by way of illustration specific embodiments in which the invention may be practiced. It is to be understood that other embodiments may be utilized and structural changes may be made without departing from the scope of the present invention and any and all changes or adaptations which may be made by those skilled in the art, are considered to be within the scope of the claimed device and method.

A wide variety and types of sensors can be used. For example, but not in a limiting fashion, one may employ proximity sensors that measure distances without requiring physical contact with the object being measured. Proximity sensing utilizes various forms of technology. All proximity sensors emit a field, and an object, often called the target, triggers the sensor when it enters the field. The type of target object dictates the kind of proximity sensor you need. Inductive proximity sensors are ideal for metallic objects while capacitive sensors detect non-metallic objects. Proximity sensors are frequently used in the security industry to control access door and gates, as well as in industrial machinery applications. Sensors typically detect a predetermined distance, called the nominal range, although some sensors allow the nominal range to be adjusted. An inductive proximity sensor operates by setting up a radio frequency field with an oscillator and a coil. When an object enters the radio frequency field, the sensor detects the alteration in the field. Inductive proximity sensors are used in various applications, including security, machine and process control, level detection and valve position.

Microwave proximity sensors aren't inhibited by distance or physical barriers. A microwave proximity sensor detects moving targets and can do so from great distances and through walls. The sensors are also used for security, as well as in applications such as paper making and textiles. A capacitive proximity sensor detects the distance between the sensor's face plate and the target object. The sensor's plate and the object function as the two capacitors, and the capacitance varies inversely with the distance between the capacitors. The operator sets the value at which the proximity sensor is triggered. Capacitive proximity sensors are capable of detecting both metallic and non-metallic targets.

Capacitive sensors most commonly function as an open capacitor. A capacitor can be best described as two conductors at different potentials, separated by an insulating material. In the capacitive sensor, these two plates, housed in the sensing head, are placed in a position such that they operate like an open capacitor. They use the air as an insulator: at rest there is little capacitance between the two plates. Like inductive sensors, these plates are linked to an oscillator, a Schmitt Trigger and an output amplifier. As a target enters the sensing range, the capacitance of the two plates increases, resulting in a change in the amplitude of the oscillator, which in turn changes the Schmitt Trigger state, thus creating an output signal. There are differences between inductive and capacitive sensors: the inductive sensor oscillates until the target is present while the capacitive does not start oscillating until the target is present. This operating principle does make the capacitive sensor a bit slower than an inductive sensor, ranging from 10 to 50 Hz. Many capacitive sensors are tubular in design with common sizes ranging from 12 to 30 mm in diameter with other housing styles available. Housing materials are usually metal and/or plastic (PBT). These are also available in shielded and unshielded mounting versions as well as normally open and normally closed. If the sensor is capable of operating as both normally open and normally closed it is said to have a "Complimentary Output." Magnetic proximity sensors are non-contact units and can be placed away from the extreme conditions they are monitoring. The units detect distance by using Hall effect principles, inductance and variable reluctance.

Preferred embodiments use sensors that have a range suitable for uses where the touching of a hand to a face of a person can be appropriately adjusted so as not to include other arm movements that would not likely cause the same risk of hand/face contact. One of skill in the art will appreciate that sensors having the physical and signal producing attributes as set forth herein can be employed for one or more specific embodiments hereof. Various appropriate sensors can be obtained from Digi Key to suit particular purposes and embodiments of the present invention. Transmission of signals may be by conventional wired or wireless communication using WiFi, Bluetooth, or Infrared signals communicating the user movements, proximity, etc.

Sensors can be associated in various embodiments with jewelry—such as rings, piercings, earrings, necklaces, bracelets, belts, bras, articles that wrap around one's waist, hats, caps, snow sports apparel, etc. Applications of the sensor units can be used, however, for all forms of human endeavor, as will be appreciated by those of skill in the art, including various use with sports teams—helmets—lacrosse, football, soccer, etc.

In certain embodiments, sensors can be used that recognize attributes of human tissue and thus are not triggered unless human tissue is present. Alternatively, sensors can be used in other embodiments (where gloves are to be worn). In such embodiments, an alarm and/or a recorder of signals can recognize differences in signals so that more accurate actual and/or potential contacts are noted.

Figure 6:
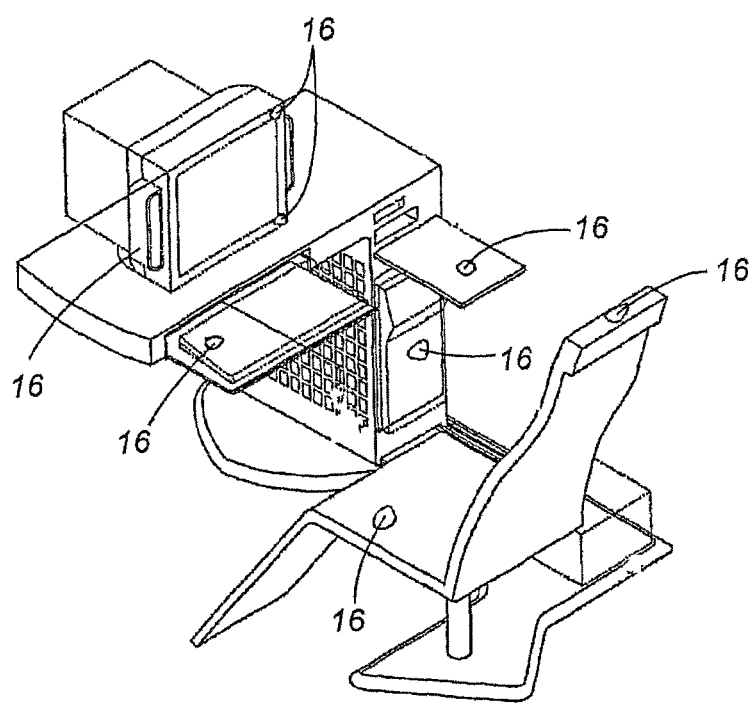
FIG. 6 shows a typical office sitting arrangement where an individual at such a work station is able to have hand to face contacts recognized through the employment of sensors positioned at various areas within such work space.
Figure 7:
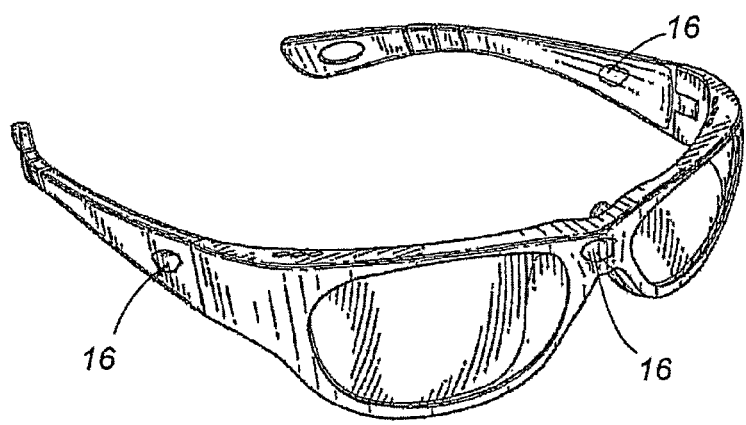
FIG. 7 shows an embodiment where sensor(s) are provided in association with a pair of glasses.

The weight of devices employed is preferably small to facilitate inconspicuous uses. Thus, weight is preferably minimal, which equates with power sources being preferably selected from watch batteries, AAA, AA, C, D, 9 volt, camera, lithium, etc. of small size and weight. In preferred embodiments, watch batteries are used to power one or more of the sensors. Some embodiments, such as those depicted in FIGS. 6 and 7, however, may not be confined by the use of small and light power sources. As such, the use of far more powerful components can be employed in such embodiments, including those associated with hearing aids.

Solar powered sensors can be used in a garment, hat, etc. to either run or recharge the sensors employed. The sensors can be associated with a wide variety of warning devices, with warnings including: light—different colors, intensity, led's, at least three different colors to indicate one of severity, duration, alarm and/or strength, sound, music, vibrations, shocks, smells, tastes, or a combination of any of the above.

Sensors may be employed to track and record the frequency of events such that a person can determine the cause therefore after the fact, especially if the conduct is separately recorded, e.g. via digital or tape recording. This permits one to fashion a training tool and procedure such that desired conduct is encouraged through a bio-feedback-like scenario. One can use devices that also record the length of contact, number of contacts in a predetermined time frame, etc. Jewelry with sensors can be used that actually changes appearance due to the number of contacts such that one can determine after a set period of time how often they may have triggered the sensor, even if audible or visual cues were not provided during actual use. In such a manner, the annoyance that may be associated with certain sensors can be avoided, and yet a follow up review of the number of contacts between hands and face can be determined in order to assess whether other measures should be taken. In various embodiments specialized jewelry is manufactured having one or more sensors such that a person's hand proximity can be detected. In other embodiments, suitable sensors can be attached to separate items that have reversibly attachable sensors so that such sensors can be attached for certain time periods or occasions and later detached. Thus, in one embodiment, sensors having adhesive components are provided in a package, preferably more than one in a package, so that a person can contact the sensor with a piece of jewelry, article of clothing (e.g., bra, hat, etc.) that is proximate the person's face and in a position such that undesired hand-to-face contact can be detected. Sensor related items may also have contact portions having anti-viral components, either Purell impregnated liquids, touchable materials.

As stated above, certain embodiments employ disposable sensor units. Others can be adapted with feathers so the sensor/recording device can be inserted directly into a computer USB port, such as a flash drive hook up, to easily provide downloaded data into computer databases. Thus, various units may be associated with a flash drive to record and track information to gauge successful use, compliance, etc. Sensors can be used of varying levels of complexity, such as those employed in TV remotes, which are capable of providing a variety of more detailed and varied possibilities with respect to modifying parameters as desired. Vibrating modes can be selected to avoid undesired noise or visual signals, thus maintaining a degree of privacy for a user.

Certain aspects of the invention are directed to a scoring system that also records hand washings, anti-bacterial soap use, nostril treatments, gargling, etc. in addition to physical contact between hands and face, thus providing a more detailed view of contamination sources, avoidance, etc. For example, teachers can use classroom competitions to see a welcomed reduction in hand to face contacts, which should directly translate to less sickness, fewer missed days of school, fewer sick days for parents, and thus, an overall tremendous economic, as well as health, benefit. Schools can utilize certain embodiments of the present invention to effectively inculcate positive and desired habits of children such that contact between hands and faces can be measured, determined and certain statistics can be derived to determine whether precautionary measures that may have been employed are deemed effective.

As children most often infect parents and parents then communicate diseases to work areas, it is particularly important that children have good habits enforced and bad habits broken. Use of the present invention can achieve such goals, often without having extended periods of use. For example, as FIG. 3 demonstrates, the very use of a sensor that indicates hand-to-face contact can significantly avert one from touching one's face in an otherwise inadvertent manner. Such cognizance of the frequency of face toughing habits is long lasting—even after removing the sensor. Thus, even sporadic uses of the devices of the present invention may have long term beneficial effects. One aspect of the present invention is therefore a method where devices described herein are not used but once a week for a period of 3 weeks, preferably 4 weeks, and even more preferably at least 5 weeks, thus forming a basis to gauge progress in reducing undesired touching of one's face. Thereafter, one may use the device to gauge compliance with certain desired or acceptable levels of touching.

In certain embodiments, the use of cell phone, so ubiquitous in our culture, can be used to signal, power, record and/or otherwise incorporate various aspects of the present invention. Ipods, iphone-like devices, etc. can have applications that make it easy for a user to have hand to face contacts recorded so that such data can be appreciated and used to reduce undesired contact. Thus, in one embodiment, one or more sensors communicate with a cell phone of a user to record or convey such data. Twitter and related social communication systems can be employed to transmit data related to the use of the variety of sensor devices described herein.

In one embodiment, the sensors interact with and transmit information to a visual device being viewed by the person, such as computer screens and TVs. For example, one embodiment involves hand-face contact being noted on the viewing screen in real time so that the person, who might otherwise not be cognizant of the fact or frequency of hand-face contact, can visualize the same. A worker in an office environment who spends the majority of their working day in front of a computer screen can be advised as to the number of times they touch their face, e.g., by a picture-in-a-picture small screen camera shot of themselves. By noting such behavior, they can then attempt to constrain such activity and form better habits that will result in health benefits being achieved. Sensors can also be employed to communicate with computer screens before which a person may sit. In certain embodiments, the person's hands can be imaged in a fashion on such screen such that the person is cognizant when a hand contacts the person's face. In addition to or instead of just imaging the contact, a signal, such as a sound, smell, vibration, shock, light, or other warning can be communicated to the person.

All electronic parts in the units used in the present invention may be sealed to prevent water intrusions using conventional means. Electrical power for the sensors, recorders, microprocessors, controllers, etc. may be provided by conventional batteries or low power transformers, as appropriate. Communication of signals from sensors to a computer, from a controller to other computers, etc. may be wired but are preferably performed by wireless means.

As some sensors require considerable power requirements, it is often advantageous to have at least one component capable of carrying more weight, such as components that have the ability to have larger battery units installed without detracting from the overall desired style and functional attributes of certain embodiments. For example, sunglasses can be fitted with cavities that can accommodate one or several batteries in a manner that the user does not object to the additional weight and volume by such batteries. Without intending to be limiting, batteries can be provided along the ear engaging portions of sunglasses and/or elsewhere in the frame, such as near the nose supporting regions.

In certain embodiments, the sensor can be focused to achieve directional sensing. In one embodiment, spectacles and/or sunglasses are provided with a sensor that interacts with another sensor provided in a ring of at least one hand. See e.g. FIG. 8. For example, in an embodiment where a sensor is positioned in the nose region of sunglasses, the sensor beam that "sees" either a hand approaching from a plane generally below a plane at or below the eye brows of an individual, can be focused to detect movement, heat, another sensor, etc. associated with a wearer's hands. In one embodiment, sunglasses incorporate two spaced sensors focused on a region within 12 inches of a person's face.

Ear bud sensors may be provided having the ability to detect the position of a person's hands, such as by either by detecting a bracelet or ring on one or both hands. Blue-tooth technology is particularly useful in various embodiments of the invention so as to minimize the use of wires and other connections that could interfere practically with the employment of the present systems and methods described herein. In one particular embodiment, such as one employing two ear bud sensors, a triangulation situation is provided with the third senor being associated with a person's hands with a sensor thereon. Other such triangulation scenarios will be apparent to one of skill in the art, but include a combination of any of three sensors being positioned in the immediate region of a person's body, such as: a belt, an earring, a necklace, ring, sunglasses, shoe, bra, shirt pants, apparel, hat, tie, etc. The work station embodiment shown in FIG. 7 can also be adapted to triangulate signals for such purpose.

Figure 4:
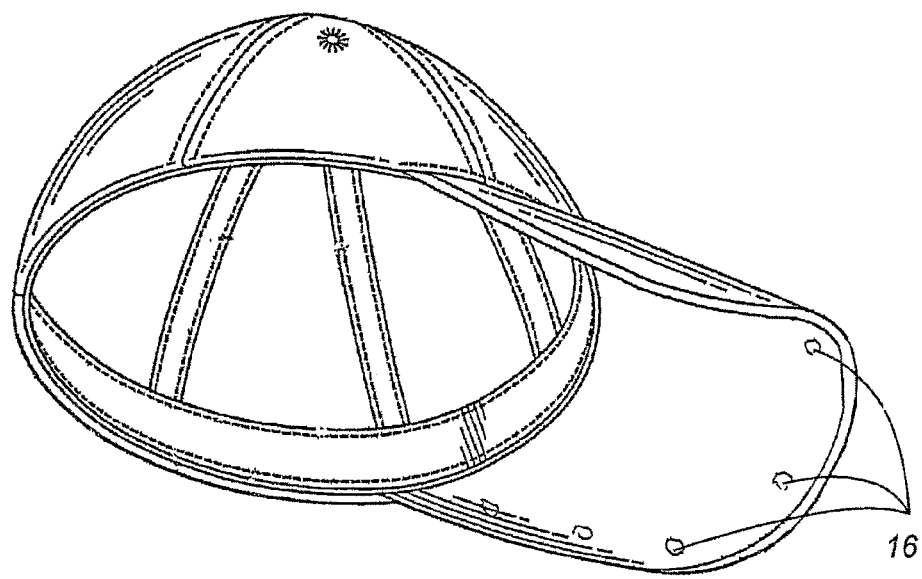
FIG. 4 is another view of a baseball cap provided with sensor(s) to detect hand to face contacts.
Figure 5:
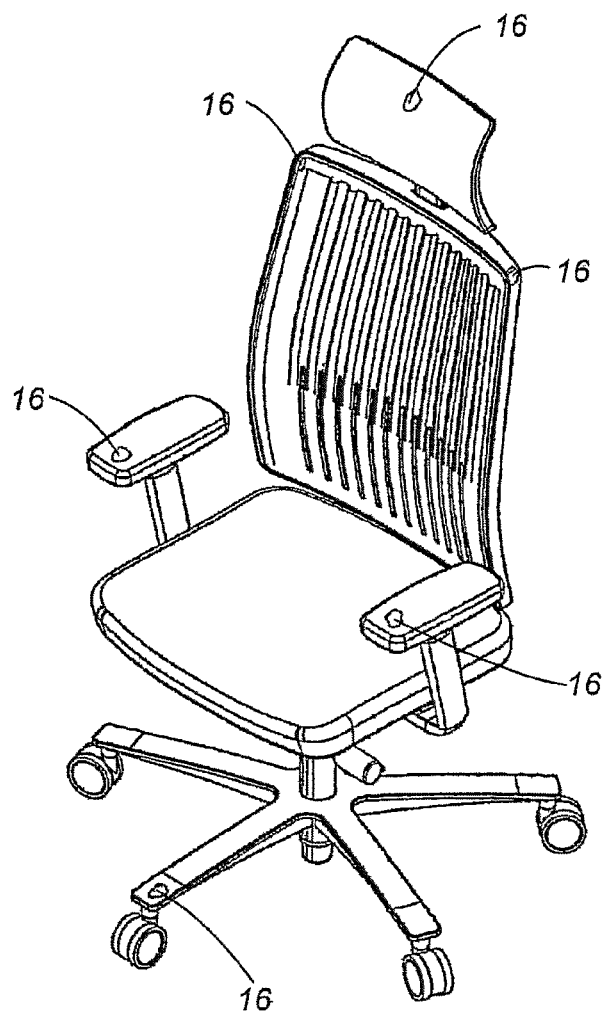
FIG. 5 shows a chair provided with sensor(s) that are positioned and fashioned in a manner such that an individual sitting in such chair can track hand to face contacts.
Figure 8:
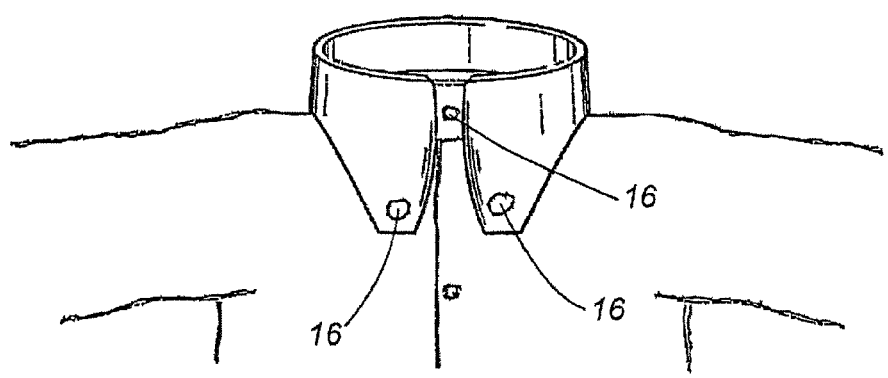
FIG. 8 shows a shirt where sensors can be positioned in various areas, such as on buttons, shirt collars, etc.
Figure 9:
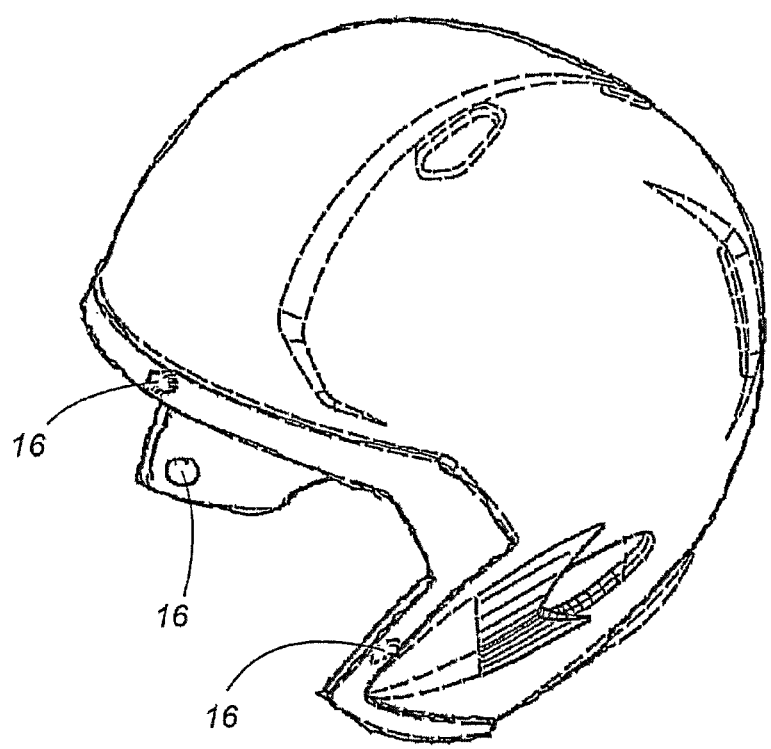
FIG. 9 shows a helmet provided with one or more sensors to detect hand to face contacts.
Figure 10:
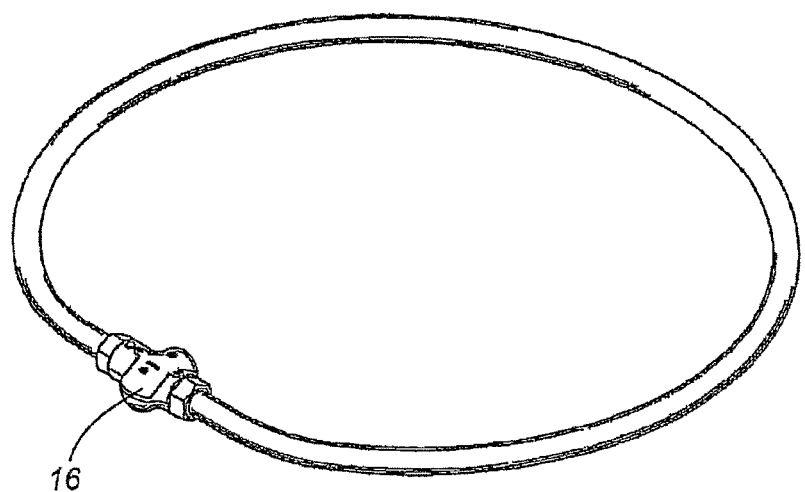
FIG. 10 shows a necklace having a senor associated therewith.
Figure 11:
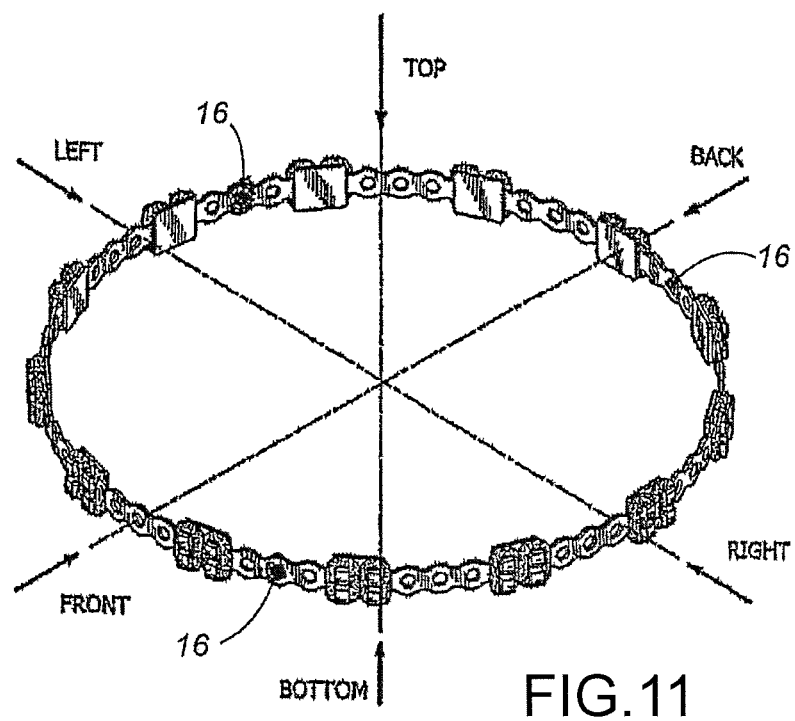
FIG. 11 shows a bracelet having one or more infrared sensitive components associated therewith.
Figure 12:
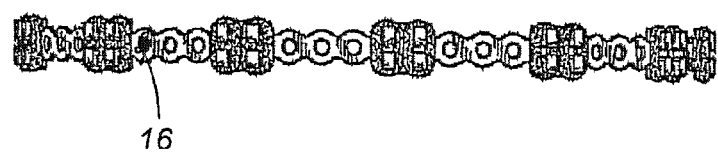
FIG. 12 is a side view of the embodiment shown in FIG. 12.
Figure 13:
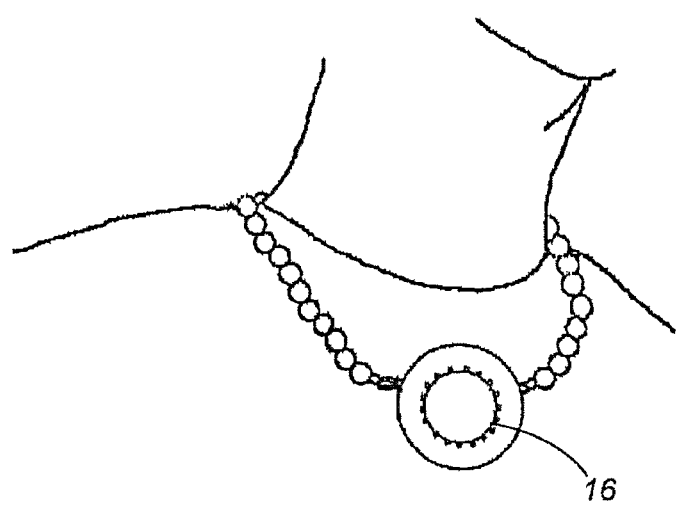
FIG. 13 shows a necklace of one embodiment of the invention with a sensor associated therewith as it would be worn by a user.
Figure 14:
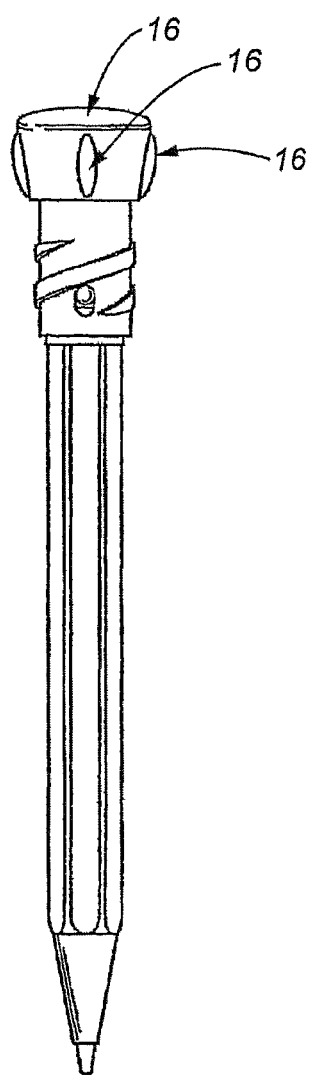
FIG. 14 shows a pen embodiment of the invention with sensors located at one end of the pen.

It is appreciated that gender differences and the willingness or desire to wear jewelry, such as a necklace, by males and females may necessitate that other means of providing a sensor in the desired area or proximity of the face should be considered. For example, FIGS. 4 and 5 are directed to caps that men may feel more comfortable in wearing, rather than some forms of jewelry. FIG. 8 is directed to glasses that employ sensors; FIG. 9 employs sensors on shirts and/or buttons; FIG. 10 shows sensors associated with helmets/headgear; and FIG. 15 shows the use of sensors on a writing instrument. More than one of these can be used at the same time to further insure that a person is appropriately warned of undesired hand/face potential contacts. One aspect of the certain embodiments relates to the ability to vary the proximity sensitivity for different environments and circumstances. For example, for different sized individuals, it may be preferred to have the proximity distance be adjusted to between 6 inches and 12 inches. For others, a longer or shorter distance may be desired. Thus, certain embodiments of the invention have tuner knobs, buttons etc. that can be employed to adjust proximity sensitivity, distance, focus, number of sensors being correlated, types, frequency or duration of signals, etc.

In yet another embodiment, the sensor employed is an IR sensor such that a beam is reflected back to a receiving sensor when an object is within the proximity region. The receiver then conveys a signal to a sound or light or vibrational unit, thus warning the user of such event. Other sensors may employ, for example heat detection, such that merely the heat of the individual's hand is sufficient to trigger the sensor. In certain embodiments sensors are utilized that require at least two separate components that communicate with each other. In other embodiments, however, sensors are employed that stand alone and can be triggered either by movement, by heat, by light interference patterns, etc. Preferably, sensors are employed using alarm systems that involve one or more of the following: sound, light, movement, vibration, electrical shock, or sense of smell.

Uses of the invention include those designed for use in airports and airplanes, which might employ reusable and/or disposable embodiments for air carrier versions that could be provided in seat for use by passengers. Sensors can also include spray detectors to detect sneezes or audible sensors to detect coughs, with such audible components toned to gauge events that may spell trouble for those susceptible to catching a disease, such as those with reduced immune responses. Such attributes can be in addition to the proximity sensors described herein.

Transmission of data collected from sensors and conveyed to remote areas, such as classrooms, so that a teacher can gauge conduct and habits of classroom as a whole, is made possible to evaluate whether certain precautions are beneficial, cost effective, etc. A city wide, state wide, and/or country wide assessment of disease spread may be critically important to evaluate global reduction of undesired hand to face touching events, which directly translates into a reduction in overall sickness of a community. The present invention makes possible the recording of hand to face touching information, tabulation of data and results, which can then be communicated to health centers to determine other possible precautionary measures. Such data, for example, may be employed by those involved in determining when, how much, what type, etc. of medications or other intervention measures may be required to forestall undesired consequences associated with impeding viral diseases, such as pandemics. The number of hand-face contacts can be used to gauge the potential for impeding health concerns as there is a direct correlation between the number of times a person touches his or her face and the occurrence of diseases communicated through physical contact between hands and face.

Components of the present invention can be combinable with shoes for battery storage or to permit use of more powerful sensors. One can employ sensors that, instead of proximity to one's face, rely on it is distance from hand to foot—such that the sensor warns when certain hand distances are exceeded, which equate with one touching their face. Components can be adjustable to different distances to accommodate different jewelry, body size and clothing of a wearer, or size of individual. Triangulation between sensors and targets may be used to appropriately focus areas of interest such as hand to face contacts.

In certain embodiments, bar coded information can be employed on jewelry, clothing, imbedded in material, etc. such that sensors can be employed that can read and track such codes for further use and evaluation. These types of readers, scanners, etc. may be used with, or instead of, proximity sensors.

One aspect of the invention can be employed in several different embodiments and includes the provision of certain IR sensitive material to rings, bracelets, appliqués, pins, Velco™-attachable items, etc. that can be associated with a person's hands fingers, etc. For example, GloTape™ is an infrared (IR) reflective material intended for the covert combat identification of troops, vehicles and equipment. To the naked eye, GloTape™ appears to be similar to black duct tape in both texture and finish without a visible reflective glow. When illuminated with an infrared diode, however, GloTape™ gives a bright reflection. The bright reflection renders the sensitivity of any device otherwise employed to be increased. The IR sensitive material referenced hereinabove can be employed on certain portions of a person's gloves, for example, ski gloves, warm weather gear, etc. when bare hands are not involved, as harmful viruses can come into contact with a person's face through contact with a gloved hand.

Appliqués can be employed in various embodiments of the invention to add or detract from the sensitivity of the sensors used. For example, in certain embodiments, one may use a sensor that is too sensitive for certain situations, such that the person may desire to decrease such sensitivity in certain regions where the sensor would otherwise be triggered. In such circumstances, counter-signals can be employed to discriminate between contact with a person's face that one desires to warn against, and other contact, such as combing or brushing one's hair, where such close proximity of a person's hand may be desired without triggering the sensor's warning.

In other embodiments, an appliqué(which can be attachable via adhesive, hook-and-loop complimentary (Velcro™ devices), snapped, buttoned, sewed, etc. can be used to increase the sensitivity of the hand-to-face interaction sought to be detected to warn the person of the same.

Sensors of particular embodiments of the invention can be contacted with jewelry that a person may already own. In such embodiments, sensors can be provided with the sensors already attached or incorporated into the item, such as jewelry (e.g. necklace, pin, earrings, sensors hidden in facial hair such as a mustache or beard, etc.) Retrofit kits for jewelry or other articles is therefore within the scope of the present invention.

In other embodiments, a combination of warning signals can be used. For example, a low powered LED can be used in combination with an adjustable sound alarm such that a person can select whether they want both type of warnings, or just one or a plurality of warnings using one or more senses. In a particular embodiment a hat brim is facilitated with a light that is viewable preferably only by the wearer thereof that lights (or alternatively, turns off, dims, blinks, etc. a light) when a hand-to face contact is about to occur.

Certain clothing can be adapted with sensors where one may not desire to wear jewelry. For example, a collar can be fitted with one or more sensors to detect when an undesired hand proximity to the face occurs. Such sensors can be positioned into existing areas that facilitate collar stays and some embodiments employ two sensors (one for each collar stay). Collar stay sensor devices can be sold separately to replace existing regular stays (such as when a shirt is laundered), thus permitting sensors to be reused, recharged, facilitated with a new battery, etc. before continued use. Such stay-like devices can similarly be employed on other items of clothing, such as headwear (e.g. hats, helmets— especially ski-helmets, football, lacrosse, etc. protective gear), coat collars, etc. due to their slim nature and ability to place such devices inside pockets that can be provided in such apparel.

Still other embodiments of the present invention include the use of one or more sensors on items closely associated with a person. Thus, in addition to the sunglasses depicted in the Figures, one will appreciate that reading glasses, goggles, other eye-protecting devices, etc. can be fitted with one or more sensors. Sensors can also be incorporated into earrings, piercings, etc. for either sex. Dental implants, capped teeth, dentures, braces, implants, retainers, etc. can be provided with one or more sensors to achieve one or more purposes as set forth in this description. Hearing aids can also be provided with sensors in a fashion that provides for such sensors to run off of the power sources used with such hearing aid devices. Wigs, toupees and hair extensions can be provided with sensors to not only provide the positioning of the sensors suitable for deterring viral, cold, etc. exposure, but specifically to address certain OCD behaviors, such as hair pulling, etc. When used in such embodiments, the sensors can be camouflaged appropriately to hide their presence in such structures. Sensors can even be provided in association with fake fingernails, rings, including particularly college and high school graduation rings (e.g. because such devices would then be naturally directed to curb the behavior patterns of young adults so as to encourage lifelong good habits, prior to becoming too old and set in one's ways.)

Another aspect of the present invention is to provide particularly directed negative feedback to a user to curb OCD behavior, including poor eating habits. Thus, in addition to the sound, visual and vibration signals, in some embodiments, the sense of smell can be employed to assist in the signaling, either alone or in combination with one or more of the other sensed signals. For example, in one embodiment, an unpleasant, and/or foul smelling agent can be released when one or more events occur. Alternatively, pleasant smells may be emitted to positively reinforce desired behavior. In certain embodiments, a sensor assembly may be adjustable by the user so that a certain minimum number of events may trigger the signal to the user. Such adjustability may include the choice of what particular type of signal is provided (e.g. whether it be based on one or more of visual, sound, smell, taste or touch-based); what frequency, duration, severity, longevity, etc. is provided for either all such predetermined events—or a set number of events prior to a or series of (same or different) signals being produced.

Many of the embodiments of the present invention are particularly directed to sensors being associated with a person's immediate body. In some embodiments, however, the sensors can be positioned remote from a person's immediate body while still achieving desired signaling and conduct-effecting behavior. For example, in addition to the office desk and vehicle environments elsewhere described herein, sensors can also be positioned around food storage places, such as a refrigerator, pantry, etc. such that the opening of the same could trigger a signal, such as an unpleasant sound, light, color, smell, vibration, etc., thus positively affecting the eating habits of individuals or groups.

One will appreciate that signals can be selected due to either positive or negative attributes. Thus, in one embodiment, a scent signal may be selected having a smell that is designed to curb one's appetite. Still other scents may be selected that have more unpleasant features, enforcing the objective of having one avoid a habitual behavior by making such conduct highly undesirable to the person, while attempting to keep such unpleasant aspects from other individuals in the same space as the individual having the sensor.

Preferably, the sensors are adjustable such that various distances can be selected by the wearer to account for different situations. For example, if a person is at a desk where their hands may be at table top level or if a person is reading a book, the distance selected for when the sensor will trigger an alarm may be set at a shorter distance than other times. In this manner, irritation with warnings due to hand proximity that is not directed toward a touching of the person's face, can be reduced and/or accommodated.

In still other embodiments, sensors can be incorporated or attached to a head covering, such as a baseball cap (e.g. in the brim) such that the proximity of a wearer's hands to the face region can be detected. In one particular embodiment, a baseball cap is provided with at least two sensors, more preferably 3 or more, and even more preferably more than 4 sensors (see FIG. 4 where 8 sensors are pictured) that can be positioned suitably around the brim such that coverage of detection of undesired hand proximity can be determined. Indeed, in one embodiment, two or more sensors can be programmed to combine their signals such that only when a suitable and predetermined signal level is decocted, the warning is communicated to the wearer or other recording device. Thus, one of skill in the art will appreciated how to use a plurality of sensors each having a sensitivity that alone may not trigger a signal warning but when two or more signals are combined and detected, the warning can be triggered.

A controller can be used, which may include an accelerometer or other motion sensor, to provide input to a computer to generate and record and process other information useful in evaluation of, for example, the number, extent, longevity, qualitative and quantitative aspects of particular contacts between a person's hands and face.

The present invention is not limited in its application to the details of construction and to the arrangement of the components set forth in the description provided or illustrated in the drawings. The invention is capable of other embodiments and of being practiced and carried out in various ways which will become obvious to those skilled in the art who read this specification. Also, it is to be understood that the phraseology and terminology employed herein are for the purpose of description and should not be regarded as limiting of the invention in any fashion.

In a preferred embodiment, every ½ second or so the device sends out a one millisecond burst of infrared pulses at 38 khz. It then looks for returned reflected signal. If the signal is detected at sufficient strength, it triggers a 600 hz signal to the speaker for one second. It then repeats the process.

One will appreciate that the above describes a simple loop. In other embodiments, the microcontroller employed can be quite powerful and versatile, such that other functions and features could easily be added. For example, in certain embodiments, only a few beeps are emitted and it then stops signaling for a while to make the device less irritable to the user. In other embodiments, a data stream is sent to another device. In still other embodiments, the number of detections over a period of time is recorded, either remotely or in proximity to the person associated with the sensor.

The more software functions added, the higher the battery drain. In one embodiment, the average power usage is 3 milliamps at 4.2 volts. Such a device can be expected to work effectively from 3.8 to 5 volts, but the sensitivity it is somewhat dependent on the battery voltage, so if different batteries are used, one may experience the device triggering at a longer range.

In one particular embodiment, certain components of the invention are as follows:

Infrared Light Emitting Diode (IR-LED): Fairchild QEC122 (Digikey QEC122-ND) 38 KHz Infrared Receiver for Remote Control: Ever light EL-IRM-8601S-1 (Mouser 638-IRM-8601S-1).

Speaker: can be a generic miniature speaker used as a signaling device in a myriad of consumer devices. There are numerous different physical shapes and sizes of these and most will work in this application. There are also "Piezo-electric" devices for this application that are very small, though they are more expensive.

Microcontroller: in one embodiment, a device includes a microcontroller such as the Parallax SX20. There are hundreds of different kinds of microcontrollers available on the market that will be understood as suitable. Two of the largest manufacturers of microcontrollers are Texas Instruments and Microchip and one who makes particular products in accordance with the invention may have their own preference based on programming issues. Preferably, the Texas Instruments MSP430 chip available from the manufacturer (www.TI.com) or from Mouser (www.mouser.com) can be favorably employed.

One will appreciate that the use of the term "sensor" in certain embodiments refers to the combination of one or more of such components. As shown in the drawings and described in detail herein discloses arrangements of elements of particular construction and configuration for illustrating preferred embodiments of structure and method of operation of the present invention. The methods disclosed herein comprise one or more steps or actions for achieving the described method. The method steps and/or actions may be interchanged with one another without departing from the scope of the present invention. In other words, unless a specific order of steps or actions is required for proper operation of the embodiment, the order and/or use of specific steps and/or actions may be modified without departing from the scope of the present invention.

With respect to various kit embodiments, the following patents are incorporated herein by this reference to demonstrate the various ways to construct kits of the present invention: U.S. Pat. No. 7,824,873 to Hale; U.S. Pat. No. 7,829,347 to Song; U.S. Pat. No. 7,829,673 to De Weeds et al.; and U.S. Pat. No. 7,785,773 to Anderson et al. al. In one particular embodiment, a kit includes a detection probe conjugated with a first specific binding member that is conFig.d to preferentially bind to the test analyte; calibration probes conjugated with a second specific binding member that is conFig.d to preferentially bind to a calibration analyte; and a lateral flow assay device on which the detection probes and calibration probes are disposed, the lateral flow assay device preferably including a porous membrane that has a detection zone in which is immobilized a first receptive material, the first receptive material being conFig.d to preferentially bind to the test analyte; an indicator zone in which is immobilized a second receptive material, the second receptive material being conFig.d to preferentially bind to uncomplexed conjugated detection probes; and a calibration zone in which is immobilized a third receptive material, the third receptive material being conFig.d to preferentially bind to the calibration analyte. The lateral flow device may further comprising a conjugate pad in fluid communication with the porous membrane and a sample pad that is positioned upstream from the conjugate pad.

Experiments

Figure 3:
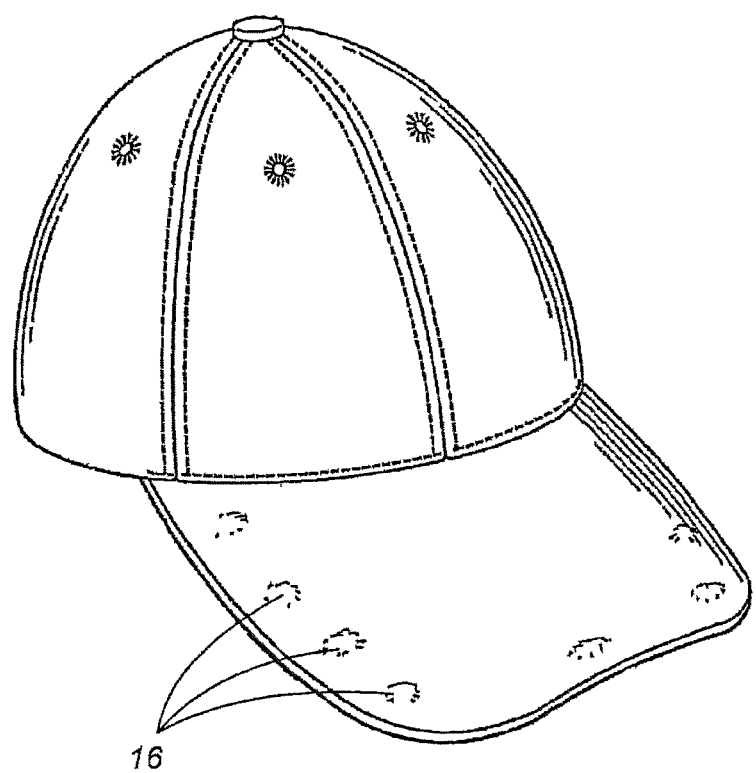
FIG. 3 is an embodiment of the invention where a baseball cap is provided with at least one sensor to detect hand to face contacts.

As depicted in FIG. 3, four individuals where videotaped for a 15 minute period without being informed as to what the purpose of such videotaping so as not to influence otherwise normal activities. The same individuals were later videotaped with a sensor hanging around their necks as a necklace for another 15 minute time period. Cart 1 displays the results that individuals generally resisted touching their faces when wearing the sensor about half as many times as they previously had when they did not wear the sensor.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception upon which this disclosure is based, may readily be utilized as a basis for designing of other structures, methods and systems for carrying out the several purposes of the present invention to instruct and encourage the avoidance of hand to face contact, thus lessening the opportunity for bacterial or virus contact with tissues that could lead to disease. It is important, therefore, that the claims be regarded as including any such equivalent construction insofar as they do not depart from the spirit and scope of the present invention.

What is claimed is:

1. A device for preventing infection by a virus, comprising:

at least two spaced apart hand movement sensors enabled to detect when a person's hand is near the person's face;

an IRED/infrared emitting device adapted to emit a signal, said IRED/infrared emitting device being operatively associated with said at least two spaced apart hand movement sensors;

a controller with a microprocessor to detect outputs of said at least two spaced apart hand movement sensors of detected movements adapted to monitor movement of a hand of a person within at least 12 inches from the face of the person, said controller with said microprocessor to detect outputs of said at least two spaced apart hand movement sensors of detected movements operatively associated with said at least two spaced apart hand movement sensors, such that when said at least two spaced apart hand movement sensors are triggered by a person's hand, said IRED/infrared emitting device emits said signal to warn a person that their hand is in the proximity of their face; and a recording transmitter for communicating from said at least two spaced apart hand movement sensors to a recording device that records the occurrence of said signal to indicate the number of hand-to-face contacts by said person, thereby reducing the risk that virus related infections will be acquired by said person, wherein said at least two spaced apart hand movement sensors are incorporated into one of a baseball cap, eye glasses and a button employed as a closure mechanism for clothing so that said two spaced apart hand movement sensors are not in contact with the person's skin.

2. The device as set forth in claim 1, wherein said IRED/infrared emitting device is adjustable with respect to an intensity of said signal.

3. The device as set forth in claim 1, wherein said emitted signal produces a sensory signal consisting of an electric shock.

4. The device as set forth in claim 1, wherein said emitted signal produces a sensory signal selected from the group consisting of a sound, a light and an electric shock.

5. The device as set forth in claim 1, wherein said emitted signal produces a sensory signal selected from the group consisting of a sound and light.

6. The device as set forth in claim 1, wherein said at least two spaced apart hand movement sensors are incorporated into a bill of a baseball cap.

7. A device for preventing infection by a virus, comprising:
- at least two spaced apart hand movement sensors enabled to detect when a person's hand is near the person's face;
- an IRED/infrared emitting device adapted to emit a signal, said IRED/infrared emitting device being operatively associated with said at least two spaced apart hand movement sensors;
- a controller with a microprocessor to detect outputs of said at least two spaced apart hand movement sensors of detected movements adapted to monitor movement of a hand of a person within at least 12 inches from the face of the person, said controller with said microprocessor to detect outputs of said at least two spaced apart hand movement sensors of detected movements operatively associated with said at least two spaced apart hand movement sensors, such that when said at least two spaced apart hand movement sensors are triggered by a person's hand, said IRED/infrared emitting device emits said signal to warn a person that their hand is in the proximity of their face; and
- a recording transmitter for communicating from said at least two spaced apart hand movement sensors to a recording device that records the occurrence of said signal to indicate the number of hand-to-face contacts by said person, thereby reducing the risk that virus related infections will be acquired by said person, wherein said at least two spaced apart hand movement sensors are incorporated into a pair of eye glasses.

8. A device for preventing infection by a virus, comprising:
- at least two spaced apart hand movement sensors enabled to detect when a person's hand is near the person's face;
- are IRED/infrared emitting device adapted to emit a signal, said IRED/infrared emitting device being operatively associated with said at least two spaced apart hand movement sensors;
- a controller with a microprocessor to detect outputs of said at least two spaced apart hand movement sensors of detected movements adapted to monitor movement of a hand of a person within at least 12 inches from the face of the person, said controller with said microprocessor to detect outputs of said at least two spaced apart hand movement sensors of detected movements operatively associated with said at least two spaced apart hand movement sensors, such that when said at least two spaced apart hand movement sensors are triggered by a person's hand, said IRED/infrared emitting device emits said signal to warn a person that their hand is in the proximity of their face; and
- a recording transmitter for communicating from said at least two spaced apart hand movement sensors to a recording device that records the occurrence of said signal to indicate the number of hand-to-face contacts by said person, thereby reducing the risk that virus related infections will be acquired by said person, wherein said at least two spaced apart hand movement sensors are incorporated into a baseball cap.

9. A device for preventing infection by a virus, comprising:
- at least two spaced apart hand movement sensors enabled to detect when a person's hand is near the person's face;
- an IRED/infrared emitting device adapted to emit a signal, said IRED/infrared emitting device being operatively associated with said at least two spaced apart hand movement sensors;
- a controller with a microprocessor to detect outputs of said at least two spaced apart hand movement sensors of detected movements adapted to monitor movement of a hand of a person within at least 12 inches from the face of the person, said controller with said microprocessor to detect outputs of said at least two spaced apart hand movement sensors of detected movements operatively associated with said at least two spaced apart hand movement sensors, such that when said at least two spaced apart hand movement sensors are triggered by a person's hand, said IRED/infrared emitting device emits said signal to warn a person that their hand is in the proximity of their face; and
- a recording transmitter for communicating from said at least two spaced apart hand movement sensors to a recording device that records the occurrence of said signal to indicate the number of hand-to-face contacts by said person, thereby reducing the risk that virus related infections will be acquired by said person, wherein said at least two spaced apart hand movement sensors are incorporated into a button employed as a closure mechanism for clothing.

\* \* \* \* \*